(12) United States Patent
Kirner et al.

(10) Patent No.: US 8,436,208 B2
(45) Date of Patent: May 7, 2013

(54) SUBSTITUTED OLIGO- OR POLYTHIOPHENES

(75) Inventors: Hans Jürg Kirner, Basel (CH); Frank Bienewald, Hegenheim (FR); Jean-Charles Flores, Mulhouse (FR); Olivier Frédéric Aebischer, Düdingen (CH)

(73) Assignee: BASF SE, Ludwigshafen (DE)

( * ) Notice: Subject to any disclaimer, the term of this patent is extended or adjusted under 35 U.S.C. 154(b) by 190 days.

(21) Appl. No.: 12/921,176

(22) PCT Filed: Mar. 6, 2009

(86) PCT No.: PCT/EP2009/052646
§ 371 (c)(1),
(2), (4) Date: Nov. 30, 2010

(87) PCT Pub. No.: WO2009/115413
PCT Pub. Date: Sep. 24, 2009

(65) Prior Publication Data
US 2011/0062426 A1 Mar. 17, 2011

(30) Foreign Application Priority Data
Mar. 17, 2008 (EP) ..................................... 08152824

(51) Int. Cl.
*C07C 233/00* (2006.01)
*C07C 235/00* (2006.01)
*C07C 237/00* (2006.01)
*C07C 239/00* (2006.01)

(52) U.S. Cl.
USPC ............. 564/199; 564/219; 564/185; 257/40; 514/304; 514/469

(58) Field of Classification Search .................. 564/199, 564/219, 185; 257/40
See application file for complete search history.

(56) References Cited

U.S. PATENT DOCUMENTS
2003/0080324 A1 5/2003 Marks et al.

FOREIGN PATENT DOCUMENTS
| EP | 1 605 007 A1 | 12/2005 |
| EP | 1 615 237 A1 | 1/2006 |
| EP | 1 679 330 A1 | 7/2006 |
| WO | 2004/058740 A1 | 7/2004 |

OTHER PUBLICATIONS

English Language abstract of WO 2004/058740 printed on Dec. 17, 2010.
Donat-Bouillud et al, Synthetic Metals 84 (1997) pp. 235-236.
Letizia et al, JACS, 130 (30), 9679-9694 (Jul. 2008).

*Primary Examiner* — Telly Green
(74) *Attorney, Agent, or Firm* — Shiela A. Loggins

(57) ABSTRACT

A process for the preparation of a substituted 2,2'-dithiophene is described, which process comprises the steps (a), (c) and optional steps (b) and (d): a reaction of a compound of the formula: with a suitable lithium organic compound, preferably Li-alkyl or Li-alkylamide; b) optional exchange of lithium against another metal selected from Mg1 Zn and Cu; c) reaction of the metallated intermediate obtained in step (a) or (b) with a suitable electrophil, which is $CO_2$ or an aldehyde (addition reaction), or a compound Y'—R17 or Y'—R18-Z (substitution reaction), where R17 and R18 are as defined in claim 1; and optionally d) modification of the product obtained in step (c), e.g. by introducing one or more conjugating moieties Y ring closure between suitable monovalent residues R17, exchange or extension of functional groups or substituents such as addition to carbonyl or substitution of carbonyl in R17 or R18. The products, including or corresponding polymers, are excellent conducting materials 18 Claims, No Drawings

SUBSTITUTED OLIGO- OR POLYTHIOPHENES

The present application relates to novel bridged 2,2'-dithiophene derivates and their use as organic semiconductor in organic devices as well as to a semiconductor device comprising said bridged dithiophene derivate.

A large number of oligo- and polythiophenes already have been prepared since exhibit interesting electronic properties, e.g. for the development of lightweight batteries, electrochromic display devices, light-emitting diodes, optical switches (see, for example, Donat-Bouillud et al., Chem. Mater. (1997) 2815).

While the properties of these compounds are widely determined by their substituents, a number of substitution patterns, such as 2,2'-dithiophenes substituted in 3,3' and/or 4,4'-positions, so far have not been easily accessible or not accessible at all.

The present invention thus pertains to a process for the preparation of a substituted 2,2'-dithiophene, which process comprises the steps
a) reaction of a compound of the formula

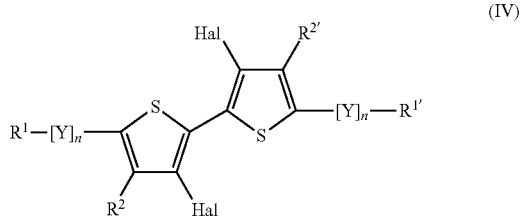

(IV)

wherein Hal stands for hydrogen or halogen, especially BrMany of the p,
R1 and R1' independently are hydrogen or a substituent,
n ranges from 0 to 6, preferably being 0;
Y, if present, is substituted or unsubstituted phenylene, thiene, 1,2-ethylene, or is 1,2-ethinylene;
R2 and R2' independently are hydrogen or are selected from $C_1$-$C_{25}$alkyl, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;
with a suitable lithium organic compound, preferably Li-alkyl or Li-alkylamide;
b) optional exchange of lithium against another metal selected from Mg, Zn and Cu by reaction with a suitable metal salt or metal organic compound; followed by
c) reaction of the metallated intermediate obtained in step (a) or (b) with a suitable electrophil, which is $CO_2$ or an aldehyde (addition reaction), or a compound Y'—R17 or Y'—R18-Z (substitution reaction), where
R17 is a suitable hydrocarbon or acyl or silyl residue,
R18 is selected from CO, CO—CO,

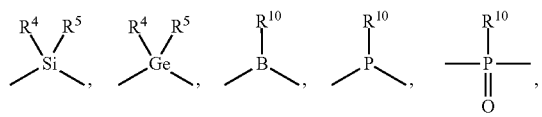

where R4, R5, and R10 are selected from $C_1$-$C_{25}$alkyl, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;

Y' and Z' are suitable leaving groups allowing for a reaction with the metal thienyl intermediate formed in step (a) or (b); and optionally
d) modification of the product obtained in step (c), e.g. by introducing one or more conjugating moieties Y as defined above, ring closure between suitable monovalent residues R17, exchange or extension of functional groups or substituents such as addition to carbonyl or substitution of carbonyl in R17 or R18.

Modification reactions as under step (d) usually are carried out in analogy to methods well known in the art.

Metal reagents for the exchange of lithium against Mg, Zn or Cu are well known in the art, examples are bromides, chlorides, iodides, carbonates, sulphates of Mg(II), Zn(II), Mn(II), Cu(II) or Cu(I). The reaction may be carried out in close analogy and under conditions known for metal exchange reactions.

An aldehyde used in the addition reaction step (c) is often selected from OCH—R20, where R20 is H or $C_1$-$C_{12}$alkyl or $C_6$-$C_{12}$aryl or -arylalkyl.

R17 as a hydrocarbon or acyl or silyl residue is often selected from
$C_1$-$C_{12}$alkyl, $C_3$-$C_{12}$cycloalkyl, $C_4$-$C_{12}$aryl, $C_5$-$C_{12}$alkylaryl or $C_5$-$C_{12}$aralkyl, $C_1$-$C_{12}$acyl, and SiRR'R" where R, R' and R" are as explained further below.

Y' and Z' as leaving groups are, independently, often selected from $C_1$-$C_{12}$alkoxy, $C_1$-$C_{12}$acyloxy, $NH_2$, $C_1$-$C_{12}$alkylamino, halogen such as iodo, or Y' and Z' are linked together to form, together with R18, a 5- or 6-membered heterocyclic ring. Preferred Y' and Z' as linked moiety include —NH—$CH_2$—$CH_2$—NH—, —O—$CH_2$—$CH_3$—O—, and substituted variants thereof.

Substituents, if present, are mainly selected from halogen, OR, $C_1$-$C_{18}$alkyl, $C_2$-$C_{18}$alkenyl, $C_1$-$C_{18}$alkylthio, $C_1$-$C_{18}$acyl, $C_4$-$C_{10}$aryl, $C_3$-$C_{12}$cycloalkyl, $C_1$-$C_{18}$acyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R", PORR', PO(OR)R', PO(OR)$_2$, PO(NHR)$_2$, PO(NRR')$_2$, CN, $NO_2$, NHR, NRR', NH—NHR, NH—NRR', CONROH;

where R, R' and R" independently are selected from $C_1$-$C_{18}$alkyl, $C_1$-$C_{18}$haloalkyl, $C_5$-$C_{10}$aryl, $C_3$-$C_{12}$cycloalkyl, preferably from $C_1$-$C_6$alkyl, phenyl, cyclopentyl, cyclohexyl; and R may also be hydrogen.

Addition of $CO_2$ in the above step (c) primarily leads to the introduction of a carboxyl function, e.g. as in the compound

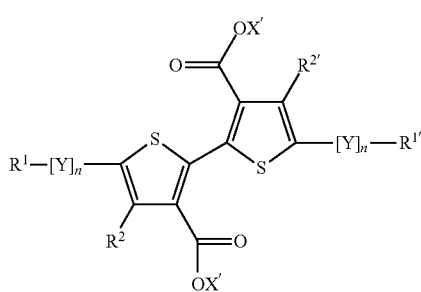

wherein X' is H or an equivalent of a cation;

addition of an aldehyde OCH—R20 leads to a hydroxylated product such as

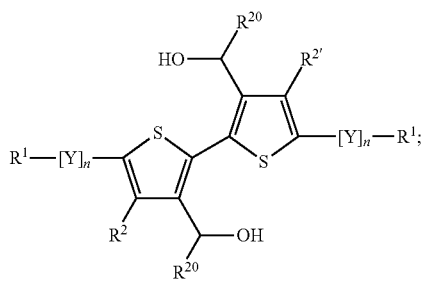

these OH or COOH functions obtained may conveniently be transformed in subsequent step (d).

Preferred products accessible by the present process are 2,2'-dithiophenes which are substituted in both positions 3,3' (or interlinked in this position to form an annelated tricyclic module), especially preferred are persubstituted end products, i.e. those which additionally carry substituents (or annellated rings) in the 4,4',5,5'-positions.

Examples for some preferred end products of the present process are those of the formulae

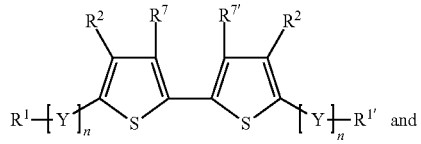
(XI)

(XII)

wherein
$R^1$ and $R^{1\prime}$ independently of each other are H or a substituent, halogen or, in case that n is not 0, may be $SiR^6R^4R^5$;
$R^2$ and $R^{2\prime}$ may be the same or different and are selected from $C_1$-$C_{25}$alkyl, $C_3$-$C_{12}$cycloalkyl, $C_2$-$C_{25}$alkenyl, $C_2$-$C_{25}$alkynyl, $C_4$-$C_{25}$aryl, $C_5$-$C_{25}$alkylaryl or $C_5$-$C_{25}$aralkyl, each of which is unsubstituted or substituted; and in case that R3 and R3', or R7 and R7', together are the bridging group

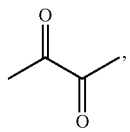

$R^2$ and $R^{2\prime}$ independently may also be hydrogen;
R4, R5, R6, R4', R5', R6' independently are selected from $C_1$-$C_{25}$alkyl, $C_3$-$C_{12}$cycloalkyl, $C_4$-$C_{25}$aryl, or $C_5$-$C_{25}$aralkyl; and the neighbouring residues R4 and R5, and correspondingly R4' and R5', may further be interlinked to form a divalent hydrocarbon residue of 4 to 25 carbon atoms which may be substituted and/or interrupted;

R3 and R3', independently, are as defined for R7, R7';
R7, R7' independently are $C_1$-$C_{25}$alkyl, $C_2$-$C_{25}$alkenyl, $C_2$-$C_{25}$alkynyl, $C_1$-$C_{25}$acyl, $C_2$-$C_{25}$alkoxycarbonyl, $C_1$-$C_{25}$acyloxy, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;
or R7 and R7', together are a bridging group selected from

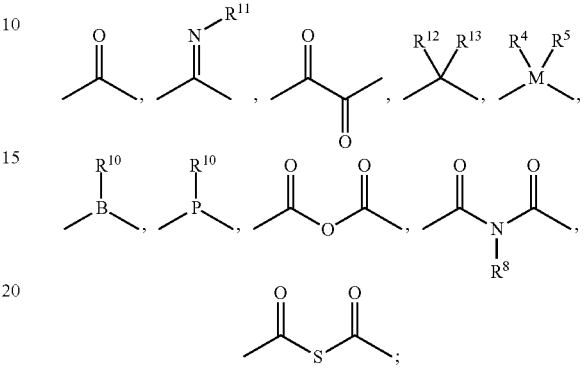

and, especially R3 and R3' together, may also form a bridging group

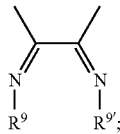

M is Si or Ge;
Y is selected from

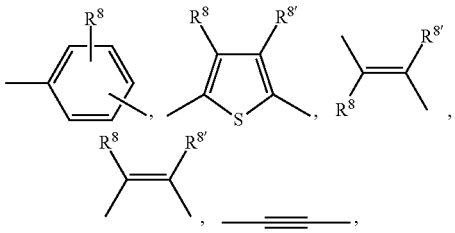

n ranges from 0 to 6;
R8 and R8' independently are H or a substituent;
R9 and R9' together form a bridging group selected from

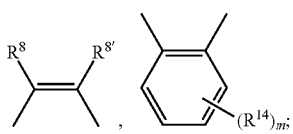

R10 is $C_1$-$C_{25}$alkyl, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;
R11 is as defined for R8 or is OR8;
one of R12 and R13 may be hydrogen while the other, or both R12 and R13, are substituents; or both R12 and R13 are interlinked to form a divalent hydrocarbon residue of 2 to 25 carbon atoms which may be substituted and/or interrupted;

m is 0, 1, 2, 3 or 4, and R14 is a substituent, or 2 or 3 neighbouring residues R14 may be interlinked to form a divalent or trivalent hydrocarbon residue of 4 to 25 carbon atoms which may be substituted and/or interrupted;

and any substituent, if present, is selected from halogen, OR, $C_1$-$C_{18}$alkyl, $C_2$-$C_{18}$alkenyl, $C_1$-$C_{18}$alkylthio, $C_1$-$C_{18}$acyl, $C_4$-$C_{10}$aryl, $C_3$-$C_{12}$cycloalkyl, $C_1$-$C_{18}$acyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R", PORR', PO(OR)R', $PO(OR)_2$, $PO(NHR)_2$, $PO(NRR')_2$, CN, $NO_2$, NHR, NRR', NH—NHR, NH—NRR', CONROH;

where R, R' and R" independently are selected from $C_1$-$C_{18}$alkyl, $C_1$-$C_{18}$haloalkyl, $C_5$-$C_{10}$aryl, $C_3$-$C_{12}$cycloalkyl, preferably from $C_1$-$C_6$alkyl, phenyl, cyclopentyl, cyclohexyl;

and R may also be hydrogen.

Products wherein R7 and R7', together, are a bridging group selected from

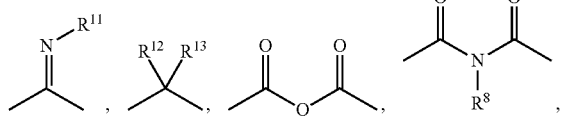

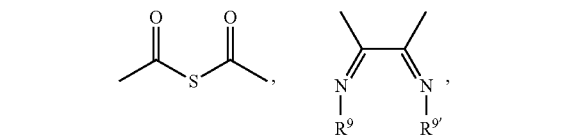

are conveniently formed in the modification/derivatization step noted above. For example, a compound containing the moiety

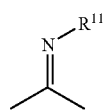

may be formed from the carbonyl precursor by reaction with an amine $H_2N$—R11;

a compound containing the moiety

may be formed from the carbonyl precursor by reaction with suitable reagents introducing R12 and R13, which lead to addition on the carbonyl-C and substitution of the OH or OR formed;

a compound containing the moiety

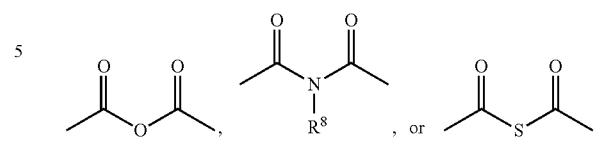

may be formed from the dicarboxy or dicarboxylate precursor described above by a suitable reaction forming an anhydride, thioanhydride or imide;

a compound containing the moiety

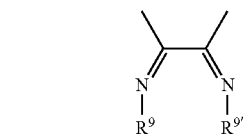

may be formed from the dicarbonyl precursor (R7 and R7' together forming the bridging group)

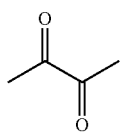

by reaction with a suitable diamine

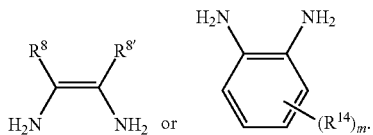

Further reaction details and transformation/modification reactions are described below and in the present examples.

In a process of special industrial interest, the intermediate obtained in step (a) or (b) from the educt compound of the formula

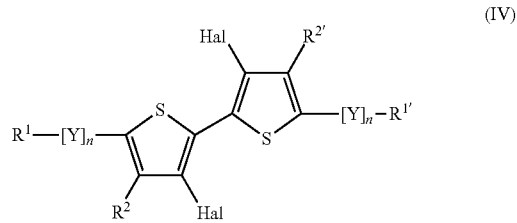

is reacted in step (c) with

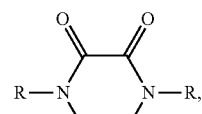

wherein R independently is as defined above, to obtain

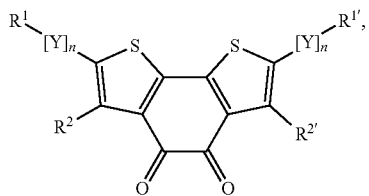

which is optionally further modified in step (d), e.g. in a manner as described above.

Some novel compounds obtained in the process of the invention have especially valuable properties for electric or electronic applications. The invention therefore includes a compound of the formula

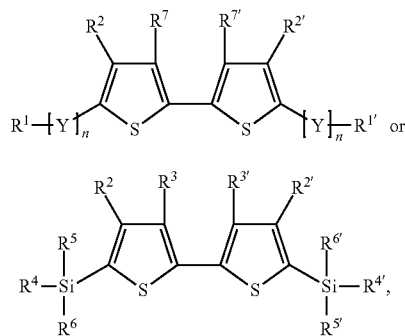

wherein
R$^1$ and R$^{1'}$ independently of each other are H or a substituent, halogen or, in case that n is not 0, may be SiR$^6$R$^4$R$^5$;
R$^2$ and R$^{2'}$ may be the same or different and are selected from C$_1$-C$_{25}$alkyl, C$_3$-C$_{12}$cycloalkyl, C$_2$-C$_{25}$alkenyl, C$_2$-C$_{25}$alkynyl, C$_4$-C$_{25}$aryl, C$_5$-C$_{25}$alkylaryl or C$_5$-C$_{25}$aralkyl, each of which is unsubstituted or substituted; and in case that R3 and R3', or R7 and R7', together are the bridging group

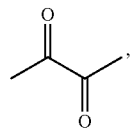

R$^2$ and R$^{2'}$ independently may also be hydrogen;
R4, R5, R6, R4', R5', R6' independently are selected from C$_1$-C$_{25}$alkyl, C$_3$-C$_{12}$cycloalkyl, C$_4$-C$_{25}$aryl, or C$_5$-C$_{25}$aralkyl; and the neighbouring residues R4 and R5, and correspondingly R4' and R5', may further be interlinked to form a divalent hydrocarbon residue of 4 to 25 carbon atoms which may be substituted and/or interrupted;
R3 and R3', independently, are as defined for R7, R7';
R7, R7' independently are C$_1$-C$_{25}$alkyl, C$_2$-C$_{25}$alkenyl, C$_2$-C$_{25}$alkynyl, C$_2$-C$_{25}$alkoxycarbonyl, C$_1$-C$_{25}$acyl, C$_1$-C$_{25}$acyloxy, C$_3$-C$_{12}$cycloalkyl, C$_4$-C$_{25}$aryl, C$_5$-C$_{25}$alkylaryl or C$_5$-C$_{25}$aralkyl, each of which is unsubstituted or substituted;

or R7 and R7', together are a bridging group selected from

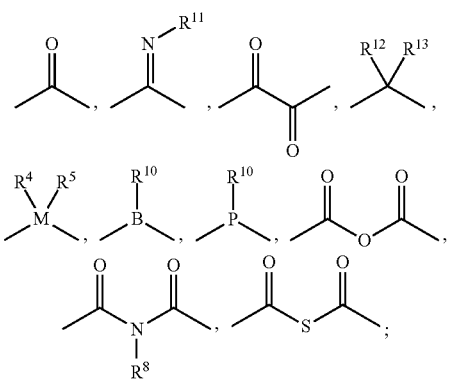

and, especially R3 and R3' together, may also form a bridging group

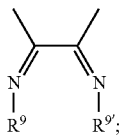

M is Si or Ge;
Y is selected from

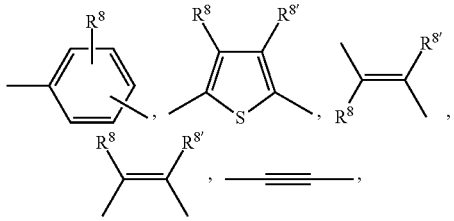

n ranges from 0 to 6;
R8 and R8' independently are H or a substituent;
R9 and R9' together form a bridging group selected from R10 is C$_1$-C$_{25}$alkyl, C$_3$-C$_{12}$cycloalkyl, C$_4$-C$_{25}$aryl, C$_5$-C$_{25}$alkylaryl or C$_5$-C$_{25}$aralkyl, each of which is unsubstituted or substituted;
R11 is as defined for R8 or is OR8;
one of R12 and R13 may be hydrogen while the other, or both R12 and R13, are substituents; or both R12 and R13 are interlinked to form a divalent hydrocarbon residue of 2 to 25 carbon atoms which may be substituted and/or interrupted;
m is 0, 1, 2, 3 or 4, and R14 is a substituent, or 2 or 3 neighbouring residues R14 may be interlinked to form a divalent or trivalent hydrocarbon residue of 4 to 25 carbon atoms which may be substituted and/or interrupted;
and
any substituent, if present, is selected from halogen, OR, C$_1$-C$_{18}$alkyl, C$_2$-C$_{18}$alkenyl, C$_1$-C$_{18}$alkylthio, C$_1$-C$_{18}$acyl, $C_4$-$C_{10}$aryl, $C_3$-$C_{12}$cycloalkyl, $C_1$-$C_{18}$acyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R", PORR', PO(OR)R', PO(OR)$_2$, PO(NHR)$_2$, PO(NRR)$_2$, CN, NO$_2$, NHR, NRR', NH—NHR, NH—NRR', CONROH;
where R, R' and R" independently are selected from $C_1$-$C_{18}$alkyl, $C_1$-$C_{18}$haloalkyl, $C_5$-$C_{10}$aryl, $C_3$-$C_{12}$cycloalkyl, preferably from $C_1$-$C_6$alkyl, phenyl, cyclopentyl, cyclohexyl;
and R may also be hydrogen;
provided that if R7 and R7' together are —CO—, at least one of R2 and R2' contains at least 2 carbon atoms, especially 4 or more carbon atoms.

R12, R13 different from hydrogen most preferably are F, $C_1$-$C_{25}$alkyl, or together are interlinked to form a divalent hydrocarbon residue of 2 to 12 carbon atoms which may be substituted and/or interrupted.

Examples of especially valuable compounds of this class conform to the formula

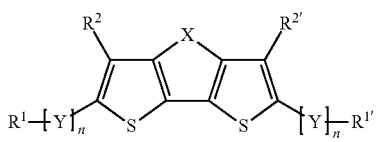

wherein
$R^1$ and $R^{1'}$ are independently of each other H, halogen or $SiR^6R^4R^5$;
$R^2$ and $R^{2'}$ may be the same or different and are selected from $C_4$-$C_{25}$alkyl, $C_2$-$C_{25}$alkenyl, $C_2$-$C_{25}$alkynyl, $C_5$-$C_{12}$cycloalkyl, $C_4$-$C_{25}$aryl, $C_5$-$C_{25}$alkylaryl or $C_5$-$C_{25}$aralkyl, each of which is unsubstituted or substituted; and in case that $R^1$ or $R^{1'}$ is $SiR^6R^4R^5$, and/or X is the bridging group

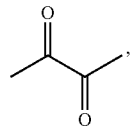

$R^2$ and $R^{2'}$ independently may also be hydrogen or $C_1$-$C_3$alkyl;
R4, R5, R6, R4', R5', R6' independently are selected from $C_1$-$C_{12}$alkyl, $C_5$-$C_{12}$cycloalkyl, phenyl, or $C_7$-$C_{12}$phenylalkyl;
X is a bridging group selected from

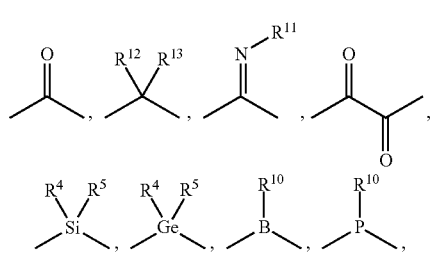

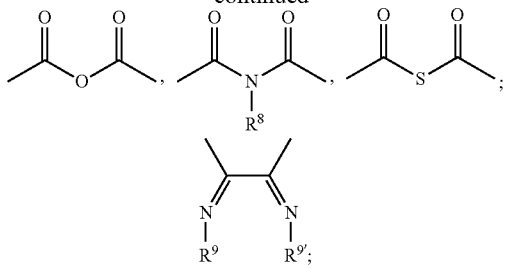

Y is selected from

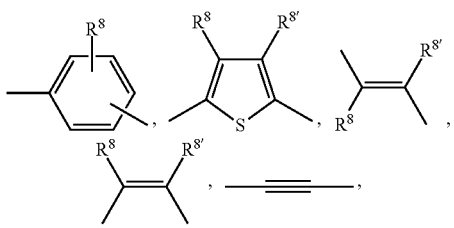

n ranges from 0 to 6;
R8 and R8' independently are H or as defined for R;
R9 and R9' together form a bridging group selected from

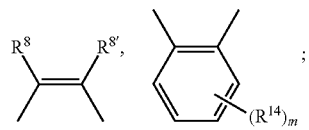

R10 is $C_1$-$C_{12}$alkyl, $C_5$-$C_{12}$cycloalkyl, phenyl, $C_7$-$C_{12}$alkylphenyl or $C_7$-$C_{12}$phenylalkyl, each of which is unsubstituted or substituted;
R11 is as defined for R8 or is OR8;
one of R12 and R13 may be hydrogen while the other, or both R12 and R13, are substituents; or both R12 and R13 are interlinked to form a divalent hydrocarbon residue of 2 to 25 carbon atoms which may be substituted and/or interrupted;
m is 0, 1, 2, 3 or 4, and R14 is a substituent, or 2 or 3 neighbouring residues R14 may be interlinked to form a divalent or trivalent hydrocarbon residue of 4 to 25 carbon atoms which may be substituted and/or interrupted; and
any substituent, if present, is selected from halogen, OR, $C_1$-$C_{18}$alkyl, $C_2$-$C_{18}$alkenyl, $C_1$-$C_{12}$alkylthio, $C_1$-$C_{18}$acyl, $C_4$-$C_{10}$aryl, $C_3$-$C_{12}$cycloalkyl, $C_1$-$C_{18}$acyloxy, $C_5$-$C_{10}$aryloxy, $C_5$-$C_{12}$cycloalkyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R", PORR', PO(OR)R', PO(OR)$_2$, PO(NHR)$_2$, PO(NRR')$_2$, CN, NO$_2$, NHR, NRR', NH—NHR, NH—NRR', CONROH;
where R, R' and R" independently are selected from $C_1$-$C_{18}$alkyl, phenyl, cyclopentyl, cyclohexyl; and R may also be hydrogen.

Preferred residues $R^1$ and $R^{1'}$ independently of each other are H, halogen or, especially in case that n is not O, $SiR^6R^4R^5$;
Some more preferred compounds are those wherein $R^1$ and $R^{1'}$ are independently of each other H, halogen or $SiR^6R^4R^5$;

$R^2$ and $R^{2'}$ may be the same or different and are selected from $C_4$-$C_{18}$alkyl or $C_5$-$C_{25}$-thienylalkyl or phenylalkyl; and in case that X is the bridging group

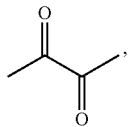

$R^2$ and $R^{2'}$, independently may also be hydrogen or $C_1$-$C_3$alkyl;
R4, R5, R6, R4', R5', R6' independently are selected from $C_1$-$C_{18}$alkyl;
R3 and R3', or R7 and R7', together, and X are a bridging group selected from

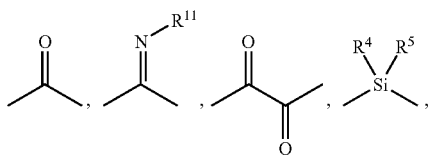

and, especially X or R3 and R3' together, may also form a bridging group

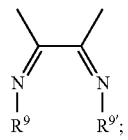

Y is

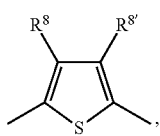

n ranges from 0 to 3;
R8 and R8' independently are H, $C_1$-$C_{18}$alkyl, phenyl, cyclopentyl, cyclohexyl;
R9 and R9' together form a bridging group selected from

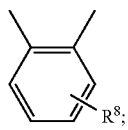

and
R11 is H, OH, $C_1$-$C_{18}$alkyl or $C_1$-$C_{18}$alkoxy.

Of special industrial interest are "symmetrical" compounds, i.e. those wherein R1=R1', both Y and indices n are identical, R2=R2', R3=R3', R4R5R6 are identical with R4'R5'R6', R7=R7' etc.

Dithiophene units as of the above formulae are well suitable as monomers for the preparation of conductive or semiconductive polymers. The invention thus further pertains to an oligomer or polymer comprising at least 2 structural units of the formula

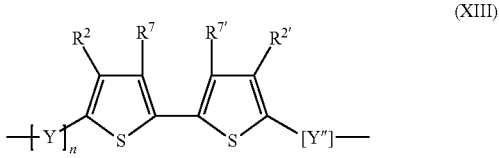

(XIII)

wherein
$R^2$ and $R^{2'}$ may be the same or different and are selected from $C_1$-$C_{25}$alkyl, $C_3$-$C_{12}$cycloalkyl, $C_2$-$C_{25}$alkenyl, $C_2$-$C_{25}$alkynyl, $C_4$-$C_{25}$aryl, $C_5$-$C_{25}$alkylaryl or $C_5$-$C_{25}$aralkyl, each of which is unsubstituted or substituted; and in case that R7 and R7', together are the bridging group

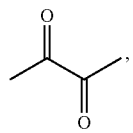

$R^2$ and $R^{2'}$ independently may also be hydrogen;
R7, R7' independently are $C_1$-$C_{25}$alkyl, $C_2$-$C_{25}$alkenyl, $C_2$-$C_{25}$alkynyl, $C_1$-$C_{25}$acyl, $C_2$-$C_{25}$alkoxycarbonyl, $C_1$-$C_{25}$acyloxy, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;
or R7 and R7', together are a bridging group selected from

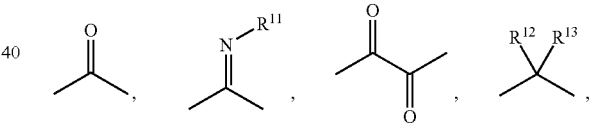

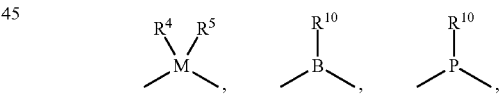

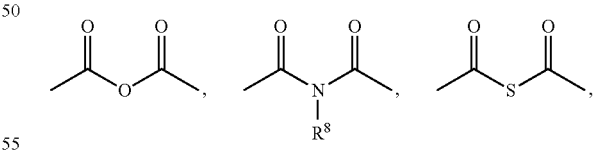

and, may also form a bridging group

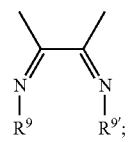

M is Si or Ge;

Y and Y" independently are selected from

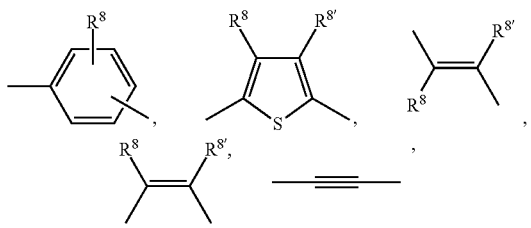

n and p independently range from 0 to 6;
R8 and R8' independently are H or a substituent;
R9 and R9' together form a bridging group selected from

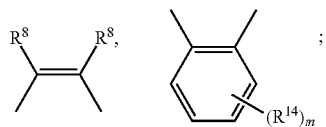

R10 is $C_1$-$C_{25}$alkyl, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;
R11 is as defined for R8 or is OR8;
one of R12 and R13 may be hydrogen while the other, or both R12 and R13, are substituents; or both R12 and R13 are interlinked to form a divalent hydrocarbon residue of 2 to 25 carbon atoms which may be substituted and/or interrupted;
m is 0, 1, 2, 3 or 4, and R14 is a substituent, or 2 or 3 neighbouring residues R14 may be interlinked to form a divalent or trivalent hydrocarbon residue of 4 to 25 carbon atoms which may be substituted and/or interrupted;
and
any substituent, if present, is selected from halogen, OR, $C_1$-$C_{18}$alkyl, $C_2$-$C_{18}$alkenyl, $C_1$-$C_{18}$alkylthio, $C_1$-$C_{18}$acyl, $C_4$-$C_{10}$aryl, $C_3$-$C_{12}$cycloalkyl, $C_1$-$C_{18}$acyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R", PORR', PO(OR)R', $PO(OR)_2$, $PO(NHR)_2$, $PO(NRR')_2$, CN, $NO_2$, NHR, NRR', NH—NHR, NH—NRR', CONROH;
where R, R' and R" independently are selected from $C_1$-$C_{18}$alkyl, $C_1$-$C_{18}$haloalkyl, $C_5$-$C_{10}$aryl, $C_3$-$C_{12}$cycloalkyl, preferably from $C_1$-$C_6$alkyl, phenyl, cyclopentyl, cyclohexyl;
and R may also be hydrogen.

Preferred oligomers or polymers of this class contain residues as defined for the dithiophenes provided by the invention and defined above.

End groups of the oligomers or polymers are usually as defined for R1 and R1' above. Besides the above structural units of the formula (XIII), oligomers or polymers of the invention may contain further monomer units, especially those useful for the preparation of electroconductive or semi-conductive polymers. The polymerization starting from suitable monomers, e.g. of present formulae (X)-(XII), may be effected in analogy to reactions described in WO08/000,664. Classes of suitable comonomer units, such as diketopyrrolopyrrole, dithiophene, and branching units, as well as methods for copolymerization, are likewise described in WO08/000,664 (see pages 5-26 therein).

Acyl stands for a residue of a sulfonic acid or especially organic carboxylic acid, which is formed formally by abstraction of the acid OH; examples are formyl, acetyl, propionyl, benzoyl. Generally, $C_1$-$C_{18}$ acyl stands for a radical X'—$R_{11}$, wherein X' is CO or $SO_2$ and $R_{11}$ is selected from monovalent aliphatic or aromatic organic residues, usually from molecular weight up to 300; for example, $R_{11}$ may be selected from $C_1$-$C_{18}$alkyl, $C_2$-$C_{18}$alkenyl, $C_5$-$C_{10}$aryl which may be unsubstituted or substituted by $C_1$-$C_8$alkyl or halogen or $C_1$-$C_8$alkoxy, $C_6$-$C_{15}$arylalkyl which may be unsubstituted or substituted in the aromatic part by $C_1$-$C_8$alkyl or halogen or $C_1$-$C_8$alkoxy, $C_4$-$C_{12}$cycloalkyl, and in case that X' is CO, $R_{11}$ may also be H. Acyl is preferably an aliphatic or aromatic residue of an organic acid —CO—$R_{11}$, usually of 1 to 30 carbon atoms, wherein $R_{11}$ embraces aryl, alkyl, alkenyl, alkynyl, cycloalkyl, each of which may be substituted or unsubstituted and/or interrupted as described elsewhere inter alia for alkyl residues, or R' may be H (i.e. COR' being formyl). Preferences consequently are as described for aryl, alkyl etc.; more preferred acyl residues are substituted or unsubstituted benzoyl, substituted or unsubstituted $C_1$-$C_{17}$alkanoyl or alkenoyl such as acetyl or propionyl or butanoyl or pentanoyl or hexanoyl, substituted or unsubstituted $C_5$-$C_{12}$cycloalkylcarbonyl such as cyclohexylcarbonyl.

Where aryl (e.g. in $C_4$-$C_{25}$aryl or $C_1$-$C_{14}$-aryl) is used, this preferably comprises monocyclic rings or polycyclic ring systems with the highest possible number of double bonds, such as preferably phenyl, naphthyl, anthrachinyl, anthracenyl or fluorenyl. The term aryl mainly embraces $C_1$-$C_{18}$aromatic moieties, which may be heterocyclic rings (also denoted as heteroaryl) containing, as part of the ring structure, one or more heteroatoms mainly selected from O, N and S; hydrocarbon aryl examples mainly are $C_6$-$C_{18}$ including phenyl, naphthyl, anthrachinyl, anthracenyl, fluorenyl, especially phenyl. Heteroaryl such as $C_1$-$C_3$heteroaryl or $C_4$-$C_{18}$heteroaryl stands for an aryl group containing at least one heteroatom, especially selected from N, O, S, among the atoms forming the aromatic ring; examples include pyridyl, pyrimidyl, pyridazyl, pyrazyl, thienyl, benzothienyl, pyrryl, furyl, benzofuryl, indyl, carbazolyl, benzotriazolyl, chinolyl, isochinolyl, triazinyl, tetrahydronaphthyl, thienyl, pyrazolyl, diazolyl, triazolyl, imidazolyl. Preferred are $C_4$-$C_{18}$aryl, e.g. selected from phenyl, naphthyl, pyridyl, tetrahydronaphthyl, furyl, thiophenyl, pyrryl, chinolyl, isochinolyl, anthrachinyl, anthracenyl, phenanthryl, pyrenyl, benzothiazolyl, benzoisothiazolyl, benzothienyl, especially $C_6$-$C_{10}$aryl; most preferred is phenyl, naphthyl, furyl, thienyl.

Halogen denotes I, Br, Cl, F, preferably Cl, Br, especially Br.

Alkyl stands for any acyclic saturated monovalent hydrocarbyl group; alkenyl denotes such a group but containing at least one carbon-carbon double bond (such as in allyl); similarly, alkynyl denotes such a group but containing at least one carbon-carbon triple bond (such as in propargyl). In case that an alkenyl or alkynyl group contains more than one double bond, these bonds usually are not cumulated, but may be arranged in an alternating order, such as in —[CH=CH—]$_n$ or —[CH=C(CH$_3$)—]$_n$, where n may be, for example, from the range 2-50. Where not defined otherwise, preferred alkyl contains 1-22 carbon atoms; preferred alkenyl and alkinyl each contains 2-22 carbon atoms, especially 3-22 carbon atoms.

Where indicated as interrupted, any alkyl moiety of more than one, especially more than 2 carbon atoms, or such alkyl or alkylene moieties which are part of another moiety, may be interrupted by a heterofunction such as O, S, COO, OCNR10, OCOO, OCONR10, NR10CNR10, or NR10, where R10 is H, $C_1$-$C_{12}$alkyl, $C_3$-$C_{12}$cycloalkyl, phenyl. They can be interrupted by one or more of these spacer groups, one group in each case being inserted, in general, into one carbon-carbon bond of the alkyl or alkylene moiety or a carbon-carbon bond the moiety is bonding to. Hetero-hetero bonds, for example O—O, S—S, NH—NH, etc., usually do not occur; if the interrupted alkyl is additionally substituted, the substituents are generally not α to the heteroatom. If two or more interrupting groups of the type —O—, —NR10-, —S— occur in one radical, they often are identical. Examples for interrupted cycloalkyls are dioxanyl, morpholinyl, piperidinyl, piperazinyl.

The term alkyl, wherever used, thus mainly embraces especially uninterrupted and, where appropriate, substituted $C_1$-$C_{22}$alkyl such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Alkoxy is alkyl-O—; alkylthio is alkyl-S—.

Haloalkyl denotes alkyl substituted by halogen; this includes perhalogenated alkyl such as perfluoroalkyl, especially $C_1$-$C_{12}$perfluoroalkyl, which is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

Aralkyl is, within the definitions given, usually selected from $C_7$-$C_{24}$aralkyl radicals, preferably $C_7$-$C_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyl-dodecyl; or phenyl-$C_1$-$C_4$alkyl substituted on the phenyl ring by one to three $C_1$-$C_4$alkyl groups, such as, for example, 2-methylbenzyl, 3-methylbenzyl, 4-methylbenzyl, 2,4-dimethylbenzyl, 2,6-dimethylbenzyl or 4-tert-butylbenzyl. or 3-methyl-5-(1',1',3',3'-tetramethyl-butyl)-benzyl.

The term alkenyl, wherever used, thus mainly embraces uninterrupted and, where appropriate, substituted $C_2$-$C_{22}$alkyl such as vinyl, allyl, etc.

Alkynyl such as $C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic cyclic moieties include cycloalkyl, aliphatic heterocyclic moieties, as well as unsaturated variants thereof such as cycloalkenyl. Cycloalkyl such as $C_3$-$C_{18}$cycloalkyl, is preferably $C_3$-$C_{12}$cycloalkyl or said cycloalkyl substituted by one to three $C_1$-$C_4$alkyl groups, and includes cyclopropyl, cyclobutyl, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred. $C_3$-$C_{12}$cycloalkyl includes cyclopropyl, cyclobutyl, cyclopentyl, cyclohexyl, cycloheptyl, cyclooctyl, cyclononyl, cyclodecyl, cycloundecyl, cyclododecyl; preferred among these residues are $C_3$-$C_6$cycloalkyl as well as cyclododecyl, especially cyclohexyl. Further ring structures occurring are heterocyclic aliphatic rings (heterocycloalkyl) usually containing 5 to 7 ring members, among them at least 1, especially 1-3, heteromoieties, usually selected from O, S, NR10, where R10 is as explained above for interrupting NR10-groups; examples include $C_4$-$C_{18}$cycloalkyl, which is interrupted by S, O, or NR10, such as piperidyl, tetrahydrofuranyl, piperazinyl and morpholinyl; examples for $C_2$-$C_4$heterocycloalkyl include oxiranyl, oxetanyl, piperazinyl, morpholinyl. Unsaturated variants may be derived from these structures by abstraction of a hydrogen atom on 2 adjacent ring members with formation of a double bond between them; an example for such a moiety is cyclohexenyl.

Alkoxy such as $C_1$-$C_{24}$alkoxy is a straight-chain or branched radical, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_6$-$C_{18}$cycloalkoxy is, for example, cyclopentyloxy, cyclohexyloxy, cycloheptyloxy or cyclooctyloxy, or said cycloalkoxy substituted by one to three $C_1$-$C_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

$C_6$-$C_{24}$aryloxy is typically phenoxy or phenoxy substituted by one to three $C_1$-$C_4$alkyl groups, such as, for example o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

$C_6$-$C_{24}$aralkoxy is typically phenyl-$C_1$-$C_9$alkoxy, such as, for example, benzyloxy, α-methylbenzyloxy, α,α-dimethylbenzyloxy or 2-phenylethoxy.

$C_1$-$C_{24}$alkylthio radicals are straight-chain or branched alkylthio radicals, such as e.g. methylthio, ethylthio, propylthio, isopropylthio, n-butylthio, isobutylthio, pentylthio, isopentyl-thio, hexylthio, heptylthio, octylthio, decylthio, tetradecylthio, hexadecylthio or octadecylthio.

Silyl such as SiRR'R" is preferably Si substituted by two or preferably three moieties selected from unsubstituted or substituted hydrocarbyl or hydrocarbyloxy (wherein the substituents are preferably other than substituted silyl), as defined above, or by unsubstituted or substituted heteroaryl. In case that Si carries only two substituents, the silyl group is of the type —SiH($R_2$) with $R_2$ preferably being hydrocarbyl or hydrocarbyloxy. Preferred hydrocarbyl(oxy) are $C_1$-$C_{20}$alkyl(oxy), aryl(oxy) such as phenyl(oxy), $C_1$-$C_9$alkylphenyl(oxy), where "(oxy)" stands for the optional linker "—O—" which may be present or not. More preferred are three $C_1$-$C_{20}$-alkyl or -alkoxy substituents, i.e. substituted silyl then is Si(R12)$_3$ with R12 being $C_1$-$C_{20}$-alkyl or -alkoxy, especially three $C_1$-$C_8$-alkyl substitutents, such as methyl, ethyl, isopropyl, t-butyl or isobutyl.

Cyclic structures formally formed by ring closure, e.g. by interlinking 2 or more adjacent residues to form a bridge such as a hydrocarbon residue of 2 to 25 carbon atoms which may be substituted and/or interrupted, often comprise 5 to 12 ring atoms in total. Examples are hydrocarbon rings such as benzene, naphthalene, anthracene, phenanthrene, cycloaliphatic rings such as $C_5$-$C_{12}$cycloalkyl, heteroaryl as explained above in more detail, or heterocyclic rings such as morpholine, piperidine, piperazine, tetrahydrofuran.

As initially mentioned, it is an object of the present invention to provide a novel approach to substituted dithiophenes.

A key step of the process of the invention relates to reactions of the intermediate 3,3'-dilithio-2,2'-dithiophene

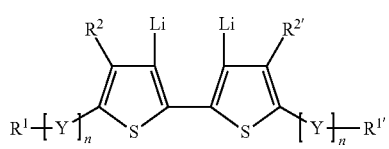
(V)

wherein the residues are as defined further above; especially preferred is the one with n=0. This intermediate is usually formed in situ, and reacted further to form the desired 3,3'-disubstituted dithiophenes, according to the following scheme:

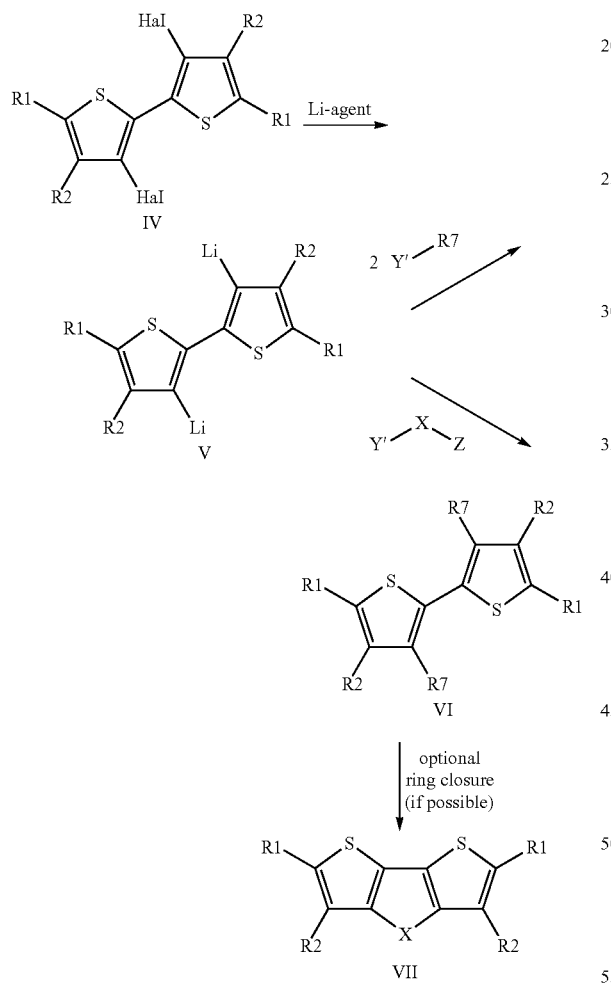

wherein Hal stands for halogen, especially Br, further residues are as defined above, where identically named residues such as R1 may be identical or different. R1 is usually different from hydrogen and preferably halogen (such as Br) or silyl (e.g. SiR4R5R6 as defined above). Y' and Z are advantageously selected from moieties able to form a covalent bond with thienyl-lithium, examples for suitable reagents Y'—R7 and Y'—X—Z are DMF, $CO_2$, esters, amides, acylchlorides, carbamoylchlorides, chlorosilanes, boronates etc. The lithiating agent may be a Li-alkyl such as butyllithium. The reactions are usually carried out in analogy to lithium reactions known in the art, e.g. under exclusion of oxygen (e.g. using $N_2$, Ar), at low temperature (e.g. −100 to 0° C.), using a suitable solvent such as ethers (diethylether, THF, dioxane etc.) or hydrocarbons (e.g. $C_5$-$C_8$alkanes).

An example is the reaction of 3,3'-dilithio-5,5'-di-trimethylsilyl-2,2'-dithiophene:

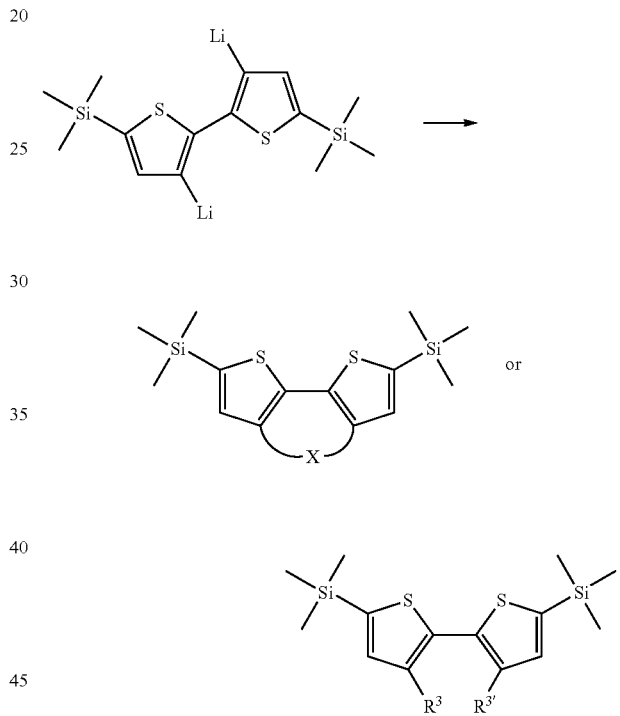

The products of the above reaction may be conveniently derivatized in close analogy to methods known in the art to obtain further compounds of the invention, e.g. by introducing one or more conjugating moieties Y, ring closure as indicated in the above scheme, exchange or extension of bridging members or substituents, polymerization to obtain homopolymers, or copolymerization with further suitable monomers as explained further above. An example for a further derivatization is given in the following scheme:

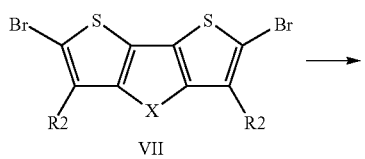

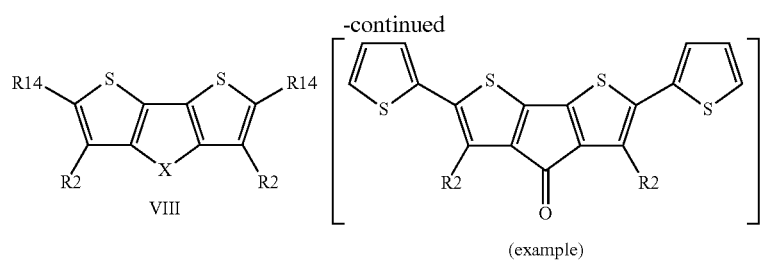
wherein R14 is preferably a residue containing one or more double bonds (YH, such as aryl, vinyl, 1-ethinyl) in conjugation with the bisthiophene moiety.
An example for a reaction sequence leading to products of the invention and embracing the novel process of the invention is outlined in the following scheme:
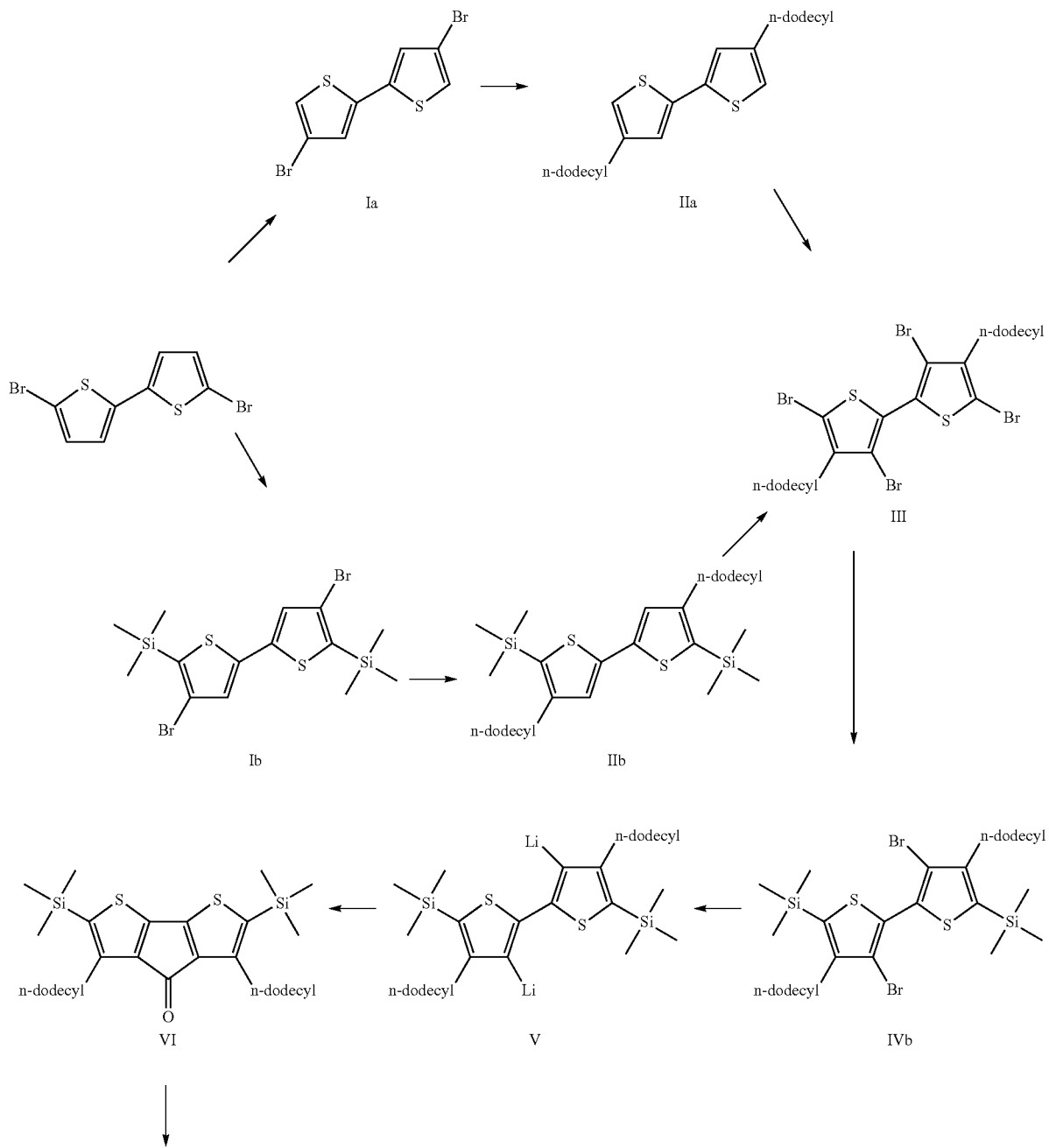

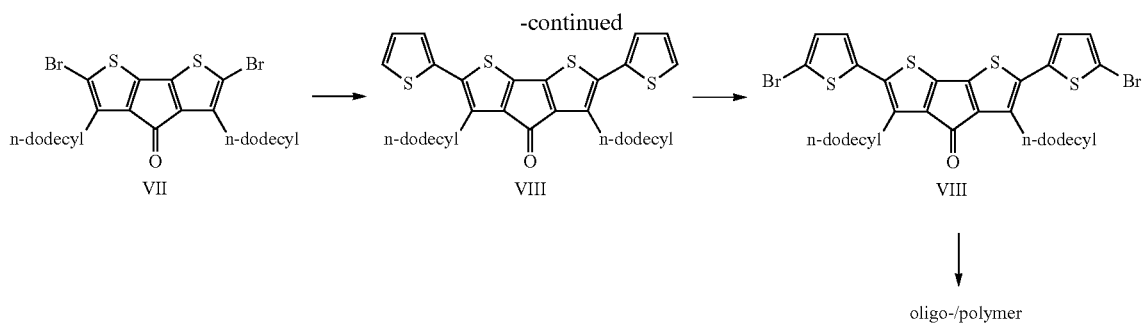

Many of the preparation methods for precursors of the present compounds are known or can be carried out in analogy to known methods. Thus, 2,2',3,3' substituted bisthiophenes may be obtained according to Bull. Soc. Chim. Belg., 1996, 615-634; an example is shown in the following scheme:

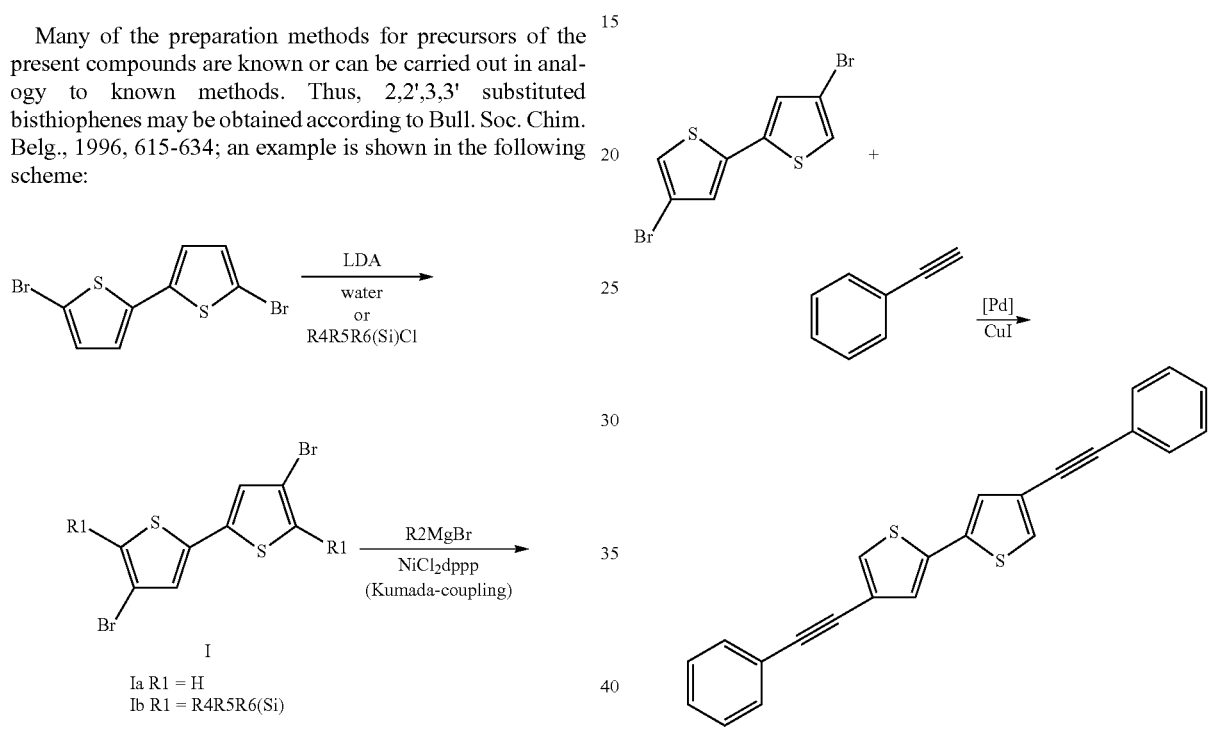

R2 may be any moiety which derives from a Grignard reagent, preferably alkyl or aryl, including Grignard compatible functional groups, or other coupling reactions like Suzuki (boronic acid derivatives) or Stille (trialkyltin derivatives), Nigishi (ZnCl derivatives); an example for a catalytic coupling reaction is the Sonogashira-coupling as described in Helv. Chim. Acta, 1996, 755-766:

wherein the ethinylbenzene reagent may be replaced by other alkynyl compounds to obtain further carbon bonded substituents R2, whose initial triple bond may be converted into a C,C double or single bond or used for the introduction of one or more substituents according to well known methods such as hydrorgenation or further addition reactions.

Alternatively, suitably substituted dithiophene precursors may be obtained from monomeric educts according to the following methods:

using at least 2 eq. of heavy metal (such as copper) for the coupling and 2 eq. of zinc for the precursor (e.g. tetrahedron letters, 2006, 2829-2833:

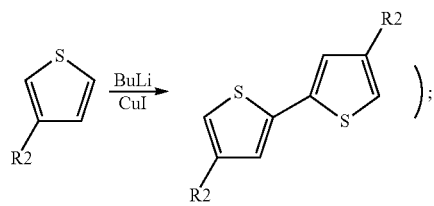

Kumada-type reactions (e.g. J. Chem. Soc. Chem. Commun, 1987, 1021-1023):

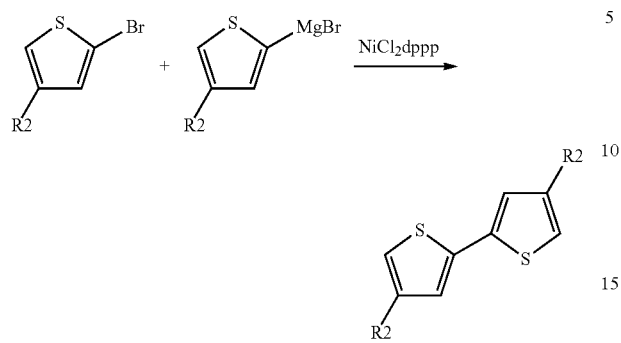

IIc may be prepared with at least 2 eq. of silver for the coupling and 2 eq. of zinc for the pre-cursor (JACS 2006, 10930-109331):

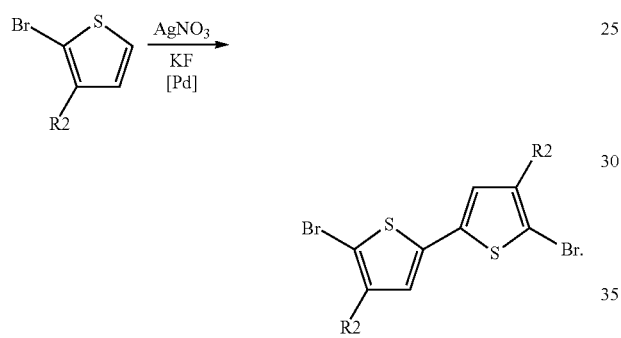

The above substances II (such as IIa or IIb) may be further converted into the corresponding 3,3',5,5'-tetrabrominated compounds III, wherein the 5-bromo may be replaced to obtain IV; an example of this reaction sequence is shown in the following scheme:

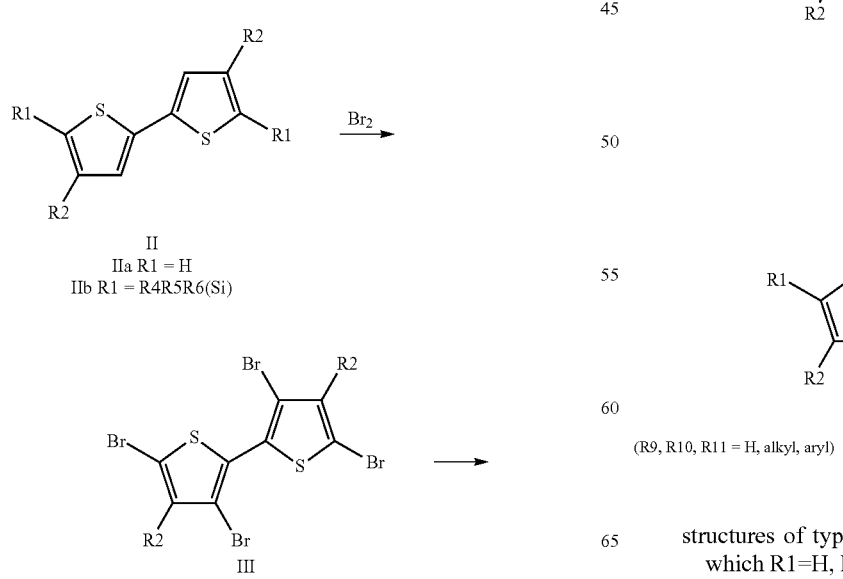

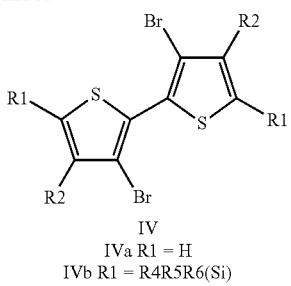

IV
IVa R1 = H
IVb R1 = R4R5R6(Si)

Preferred examples for compounds of the invention include those
of type VI, derived from V, in which R1=H, Br or silyl and all other R mean C-substitution, e.g. of the formulae:

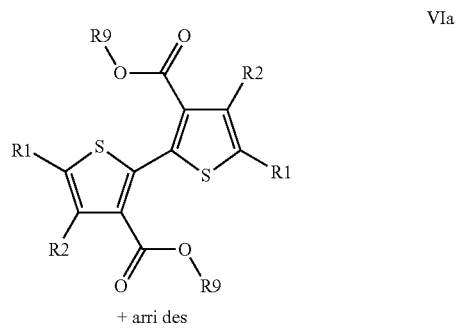

VIa

+ arri des

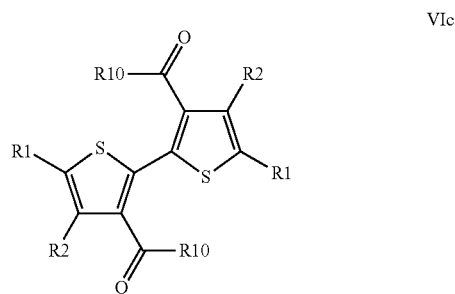

VIc

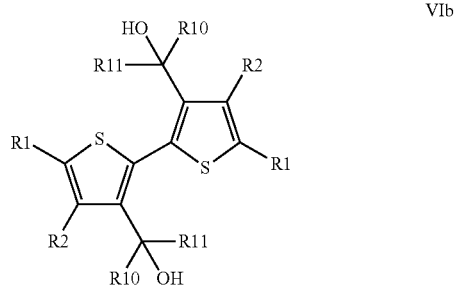

VIb (R9, R10, R11 = H, alkyl, aryl)

structures of type VII, derived from V as claimed, in which R1=H, Br or silyl and all other R mean C-substitution, preferred examples:

Heterocycles

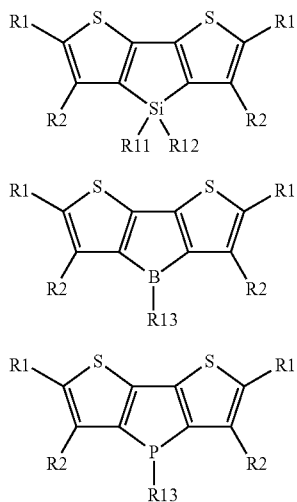

Cycles derived from structures of type VI

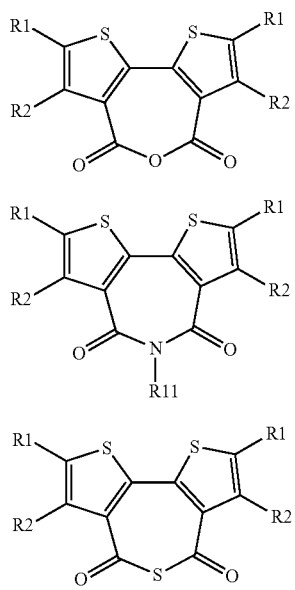

Introduction of a silyl R2 groups may, for example, follow the following scheme:

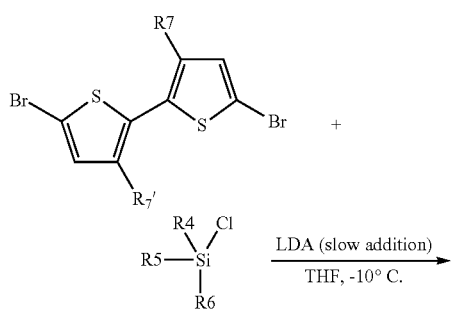

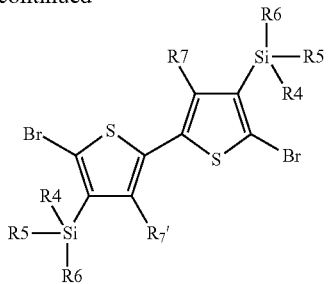

The compounds and polymers of the invention can be used as the semiconductor layer in semiconductor devices. Accordingly, the present invention also relates to semiconductor devices, comprising a compound of formulae (XI), (XII) and/or an oligo/polymer of the formula (XIII). The semiconductor device is especially a diode, an organic field effect transistor and/or a solar cell, or a device containing a diode and/or an organic field effect transistor, and/or a solar cell. There are numerous types of semiconductor devices. Common to all is the presence of one or more semiconductor materials. Semiconductor devices have been described, for example, by S. M. Sze in Physics of Semiconductor Devices, $2^{nd}$ edition, John Wiley and Sons, New York (1981). Such devices include rectifiers, transistors (of which there are many types, including p-n-p, n-p-n, and thin-film transistors), light emitting semiconductor devices (for example, organic light emitting diodes in display applications or backlight in e.g. liquid crystal displays), photoconductors, current limiters, solar cells, thermistors, p-n junctions, field-effect diodes, Schottky diodes, and so forth. In each semiconductor device, the semiconductor material is combined with one or more metals and/or insulators to form the device. Semiconductor devices can be prepared or manufactured by known methods such as, for example, those described by Peter Van Zant in Microchip Fabrication, Fourth Edition, McGraw-Hill, New York (2000). In particular, organic electronic components can be manufactured as described by D. R. Gamota et al. in Printed Organic and Molecular Electronics, Kluver Academic Publ., Boston, 2004.

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, 2.sup.nd edition, John Wiley and Sons, page 492, New York (1981)). These components can be assembled in a variety of configurations such as top-gate, bottom-gate or as vertical transistor. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise silicon materials inclusive of various appropriate forms of silicon, inorganic glasses, ceramic foils, polymeric materials (for example, acrylics, polyester, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly (ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive oxides, such as indium tin oxide, or conducting inks/pastes comprised of carbon black/graphite or colloidal silver dispersions, optionally containing polymer binders can also be used. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material.

The gate dielectric (insulator) can be a material, such as, an oxide, nitride, or it can be a material selected from the family of ferroelectric insulators (e.g. organic materials such as poly (vinylidene fluoride/trifluoroethylene or poly(m-xylylene adipamide)), or it can be an organic polymeric insulator (e.g. poly(methacrylate)s, poly(acrylate)s, polyimides, benzocyclobutenes (BCBs), parylenes, polyvinylalcohol, polyvinylphenol (PVP), polystyrenes, polyester, polycarbonates) as for example described in J. Veres et al. Chem. Mat. 2004, 16, 4543 or A. Facchetti et al. Adv. Mat. 2005, 17, 1705. Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulphide, including but not limited to $PbZr_xTi_{1-x}O_3$ (PZT), $Bi_4Ti_3O_{12}$, $BaMgF_4$, $Ba(Zr_{1-x}Ti_x)O_3$ (BZT). In addition, alloys, hybride materials (e.g. polysiloxanes or nanoparticle-filled polymers) combinations, and multilayers of these materials can be used for the gate dielectric. The thickness of the dielectric layer is, for example, from about 10 to 1000 nm, with a more specific thickness being about 100 to 500 nm, providing a capacitance in the range of 0.1-100 nanofarads (nF).

The source electrode and drain electrode are separated from the gate electrode by the gate dielectric, while the organic semiconductor layer can be over or under the source electrode and drain electrode. The source and drain electrodes can be any useful conductive material favourably providing a low resistance ohmic contact to the semiconductor layer. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art. In order to improve charge injection, various methods for doping the electrode(surface) have been described in the literature.

The thin film electrodes (that is, the gate electrode, the source electrode, and the drain electrode) can be provided by any useful means such as physical vapor deposition (for example, thermal evaporation or sputtering) or (ink jet) printing methods. The patterning of these electrodes can be accomplished by known methods such as shadow masking, additive photolithography, subtractive photolithography, printing, microcontact printing, and pattern coating.

The present invention further provides a thin film transistor device comprising
a plurality of electrically conducting gate electrodes disposed on a substrate;
a gate insulator layer disposed on said electrically conducting gate electrodes;
a plurality of sets of electrically conductive source and drain electrodes disposed on said insulator layer such that each of said sets is in alignment with each of said gate electrodes;
an organic semiconductor layer disposed in the channel between source and drain electrodes on said insulator layer substantially overlapping said gate electrodes; wherein said organic semiconductor layer comprise a compound of formulae (XI), (XII) and/or an oligo/polymer of the formula (XIII), or a mixture containing one or more such compounds.

The present invention further provides a process for preparing a thin film transistor device comprising the steps of:
depositing a plurality of electrically conducting gate electrodes on a substrate;
depositing a gate insulator layer on said electrically conducting gate electrodes;
depositing a plurality of sets of electrically conductive source and drain electrodes on said layer such that each of said sets is in alignment with each of said gate electrodes;
depositing a layer of a compound of formulae (XI), (XII) and/or an oligo/polymer of the formula (XIII) on said insulator layer such that said layer of the compound of the invention, or mixture containing such a compound, substantially overlaps said gate electrodes; thereby producing the thin film transistor device.

A mixture containing a compound of formulae (XI), (XII) and/or an oligo/polymer of the formula (XIII) results in a semi-conducting layer comprising a compound of formulae (XI), (XII) and/or an oligo/polymer of the formula (XIII) (typically 5% to 99.9999% by weight, especially 20 to 85% by weight) and at least another material. The other material can be, but is not restricted to a fraction of the same polymer of formula (XIII) with different molecular weight, another compound of the invention, a semi-conducting polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.).

For heterojunction solar cells the active layer comprises preferably a mixture of a polymer of formula I and a fullerene, such as [60]PCBM (=6,6-phenyl-C61-butyric acid methyl ester), or [70]PCBM, in a weight ratio of 1:1 to 1:3.

Any suitable substrate can be used to prepare the thin films of the compounds and/or polymers of the present invention. Preferably, the substrate used to prepare the above thin films is a metal, silicon, plastic, paper, coated paper, fabric, glass or coated glass.

Alternatively, a TFT is fabricated, for example, by solution deposition of a compound and/or polymer of the invention on a highly doped silicon substrate covered with a thermally grown oxide layer followed by vacuum deposition and patterning of source and drain electrodes.

In yet another approach, a TFT is fabricated by deposition of source and drain electrodes on a highly doped silicon substrate covered with a thermally grown oxide and then solution deposition of the compound and/or polymer to form a thin film.

The gate electrode could also be a patterned metal gate electrode on a substrate or a conducting material such as, a conducting polymer, which is then coated with an insulator applied either by solution coating or by vacuum deposition on the patterned gate electrodes.

Any suitable solvent can be used to dissolve, and/or disperse the compounds and/or polymers of the present invention, provided it is inert and can be removed partly, or completely, from the substrate by conventional drying means (e.g. application of heat, reduced pressure, airflow etc.). Suitable organic solvents for processing the semiconductors of the invention include, but are not limited to, aromatic or aliphatic hydrocarbons, halogenated such as chlorinated or fluorinated hydrocarbons, esters, ethers amides, such as chloroform, tetrachloroethane, tetrahydrofuran, toluene, tetraline, anisole, xylene, ethyl acetate, methyl ethyl ketone, dimethyl formamide, dichlorobenzene, trichlorobenzene, propylene glycol monomethyl ether acetate (PGMEA) and mixtures thereof. The solution, and/or dispersion is then applied by a method, such as, spin-coating, dip-coating, screen printing, microcontact printing, doctor blading or other solution application techniques known in the art on the substrate to obtain thin films of the semiconducting material.

The term "dispersion" covers any composition comprising the semiconductor material of the present invention, which is not fully dissolved in a solvent. The dispersion can be done selecting a composition including at least a compound of formulae (XI), (XII) and/or an oligo/polymer of the formula (XIII), or a mixture containing such a compound, and a solvent, wherein the compound/polymer exhibits lower solubility in the solvent at room temperature but exhibits greater solubility in the solvent at an elevated temperature, wherein the composition gels when the elevated temperature is lowered to a first lower temperature without agitation;

dissolving at the elevated temperature at least a portion of the compound/polymer in the solvent; lowering the temperature of the composition from the elevated temperature to the first lower temperature; agitating the composition to disrupt any gelling, wherein the agitating commences at any time prior to, simultaneous with, or subsequent to the lowering the elevated temperature of the composition to the first lower temperature; depositing a layer of the composition wherein the composition is at a second lower temperature lower than the elevated temperature; and drying at least partially the layer.

The dispersion can also be constituted of (a) a continuous phase comprising a solvent, a binder resin, and optionally a dispersing agent, and (b) a disperse phase comprising a compound of formulae (XI), (XII) and/or an oligo/polymer of the formula (XIII), or mixture containing a compound and/or polymer of the present invention. The degree of solubility of the present compound/polymer in the solvent may vary for example from 0% to about 20% solubility, particularly from 0% to about 5% solubility.

Preferably, the thickness of the organic semiconductor layer is in the range of from about 5 to about 1000 nm, especially the thickness is in the range of from about 10 to about 100 nm.

The compounds/polymers of the invention can be used alone or in combination as the organic semiconductor layer of the semiconductor device. The layer can be provided by any useful means, such as, for example, vapor deposition (for materials with relatively low molecular weight) and printing techniques. The compounds of the invention may be sufficiently soluble in organic solvents and can be solution deposited and patterned (for example, by spin coating, dip coating, ink jet printing, gravure printing, flexo printing, offset printing, screen printing, microcontact (wave)-printing, drop or zone casting, or other known techniques).

The compounds/polymers of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like. Due to its ambi-polarity the material can also be used in Organic Light Emitting Transistors (OLET).

The invention provides organic photovoltaic (PV) devices (solar cells) comprising a polymer according to the present invention.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the polymers of the present invention. Preferably, the photoactive layer is made of a conjugated polymer of the present invention, as an electron donor and an acceptor material, like a fullerene, particularly a functionalized fullerene PCBM, as an electron acceptor.

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another compound and/or polymer of present invention or any semi-conducting polymer provided that the polymers retain acceptor-type and electron mobility characteristics, organic small molecules, carbon nanotubes, inorganic particles (quantum dots, quantum rods, quantum tripods, $TiO_2$, ZnO etc.).

The electrodes are preferably composed of metals or "metal substitutes". Herein the term "metal" is used to embrace both materials composed of an elementally pure metal, e.g., Mg, and also metal alloys which are materials composed of two or more elementally pure metals, e.g., Mg and Ag together, denoted Mg:Ag. Here, the term "metal substitute" refers to a material that is not a metal within the normal definition, but which has the metal-like properties that are desired in certain appropriate applications. An example is a printable conductive ink, as described in WO08/135,632. Commonly used metal substitutes for electrodes and charge transfer layers would include doped wide-bandgap semiconductors, for example, transparent conducting oxides such as indium tin oxide (ITO), gallium indium tin oxide (GITO), and zinc indium tin oxide (ZITO). Another suitable metal substitute is the transparent conductive polymer polyanaline (PANI) and its chemical relatives, or PEDOT:PSS. Metal substitutes may be further selected from a wide range of non-metallic materials, wherein the term "non-metallic" is meant to embrace a wide range of materials provided that the material is free of metal in its chemically uncombined form. Highly transparent, non-metallic, low resistance cathodes or highly efficient, low resistance metallic/non-metallic compound cathodes are, for example, disclosed in U.S. Pat. No. 6,420,031 and U.S. Pat. No. 5,703,436.

The substrate can be, for example, a plastic (flexible substrate), or glass substrate.

In another preferred embodiment of the invention, a smoothing layer is situated between the anode and the photoactive layer. A preferred material for this smoothing layer comprises a film of 3,4-polyethylenedioxythiophene (PEDOT), or 3,4-polyethylenedioxythiophene:polystyrene-sulfonate (PEDOT:PSS).

In a preferred embodiment of the present invention, the photovoltaic cell comprises, as described for example, in U.S. Pat. No. 6,933,436 a transparent glass carrier, onto which an electrode layer made of indium/tin oxide (ITO) is applied. This electrode layer generally has a comparatively rough surface structure, so that it is covered with a smoothing layer made of a polymer, typically PEDOT, which is made electrically conductive through doping. The photoactive layer is made of two components, has a layer thickness of, for example, 100 nm to a few µm depending on the application method, and is applied onto this smoothing layer. Photoactive layer is made of a conjugated compound and/or polymer of the present invention, as an electron donor and a fullerene, particularly functionalized fullerene PCBM, as an electron acceptor. These two components are mixed with a solvent and applied as a solution onto the smoothing layer by, for example, the spin-coating method, the casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

Before a counter electrode is applied, a thin transition layer, which must be electrically insulating, having a layer thickness of, for example, 0.6 nm, is applied to photoactive layer 4. In this exemplary embodiment, this transition layer is made of an alkali halogenide, namely a lithium fluoride, which is vapor deposited in a vacuum of $2 \cdot 10^{-6}$ torr at a rate of 0.2 nm/minute.

If ITO is used as a hole-collecting electrode, aluminum, which is vapor deposited onto the electrically insulating transition layer, is used as an electron-collecting electrode. The electric insulation properties of the transition layer obviously prevent influences which hinder the crossing of the charge carrier from being effective, particularly in the transition region from the photoactive layer to the transition layer.

In a further embodiment on the invention, one or more of the layers may be treated with plasma prior to depositing the next layer. It is particularly advantageous that the PEDOT:PSS layer be subject to a mild plasma treatment prior to deposition of the next layer.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the inventive compounds, materials or films can also be used alone or together with other materials in or as alignment layers in LCD or OLED devices, as described for example in US2003/0021913.

The following examples are included for illustrative purposes only and are not to be construed to limit the scope of the claims. Unless otherwise stated, all parts and percentages are by weight. Room temperature denotes a range 18-23° C.; analytical data are compiled in the table at the end of the preparation examples. Abbreviations:
NBS N-bromosuccinimide
LDA Lithium diisopropylamide

EXAMPLES

Example 1

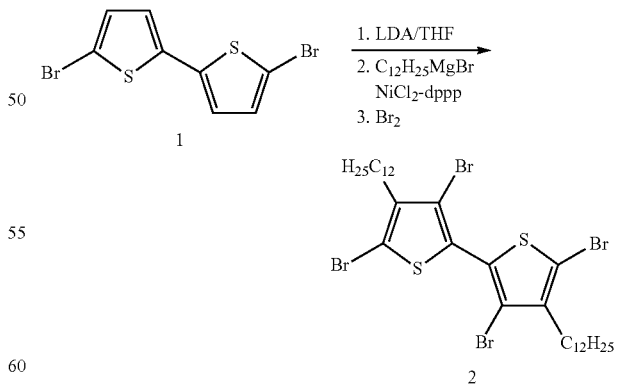

a) A solution of 40 g of 1 in 200 ml of dry tetrahydrofuran (THF) is added rapidly to a solution of lithium diisopropylamide (LDA, prepared from 100 ml of 2.7 M solution of butyllithium in hexane and 28.8 g diisopropylamine in 200 ml of dry THF) at −70° C. under nitrogen atmosphere. After the colour of the mixture has become orange-brown, the mixture is allowed to warm to −20° C. and then 100 ml of water are added. The organic phase is separated, washed with brine, dried and evaporated. The residue is recrystallized from methanol to obtain 36.5 g of 4,4'-dibromo-2,2'-dithiophene as an off-white powder (yield: 91.2%).

A solution of n-dodecyl magnesium bromide in ether (prepared from 9 g of magnesium turnings and 87.0 g n-dodecylbromide in 200 ml of diethylether) is slowly added to a solution of 40 g of 4,4'-dibromo-2,2'-dithiophene. 1 mol % NiCl$_2$(dppp) (dppp=Ph$_2$PCH$_2$CH$_2$CH$_2$PPh$_2$) in 200 ml of diethylether is added in such a way, that the internal temperature does not exceed 20° C. Then the mixture is stirred at room temperature for 2 hours and 200 ml of water are added thereto. The organic phase is separated, washed with diluted hydrochloric acid and brine, dried and evaporated. The residue is suspended in methanol and 55.8 g of 4,4'-n-didodecyl-2,2-dithiophene is obtained as a beige powder by filtation (yield: 70%).

12.8 g of bromine are added dropwise to a solution of 10.1 g 4,4'-n-didodecyl-2,2-dithiophene in 100 ml chloroform and 40 ml acetic acid at 0° C. under nitrogen atmosphere. The mixture is heated at 60° C. for 16 hours. After cooling to room temperature the mixture is treated with 50 ml of a saturated solution of sodium sulfite. The organic phase is separated, washed with a saturated aqueous solution of sodium hydrogen carbonate and brine, dried and evaporated. The residue is suspended in methanol and 14.5 g of 2 is obtained as a beige powder by filtration (yield: 88.4%).

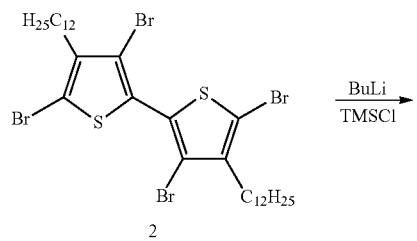

2

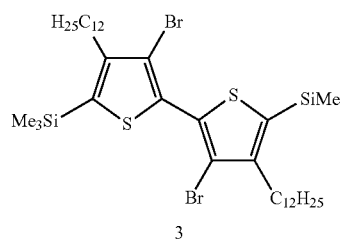

3 b) 10 g of 2 are dissolved in 150 ml dry THF and 70 ml heptane under nitrogen atmosphere and the solution is cooled to −20° C. After adding of 9.5 ml of a 2.7 M solution of butyllithium in heptane the obtained solution is stirred at −20° C. for 1 hour, 3 ml of trimethylsilyl chloride (TMSCl) is added thereto, the resulting mixture is stirred at −20° for 15 minutes and then allowed to warm to room temperature. After stirring for an additional hour 50 ml of water are added. The organic phase is separated, washed with brine, dried and evaporated to obtain 9.9 g of 3 as an orange-brown semisolid residue (yield: 100%).

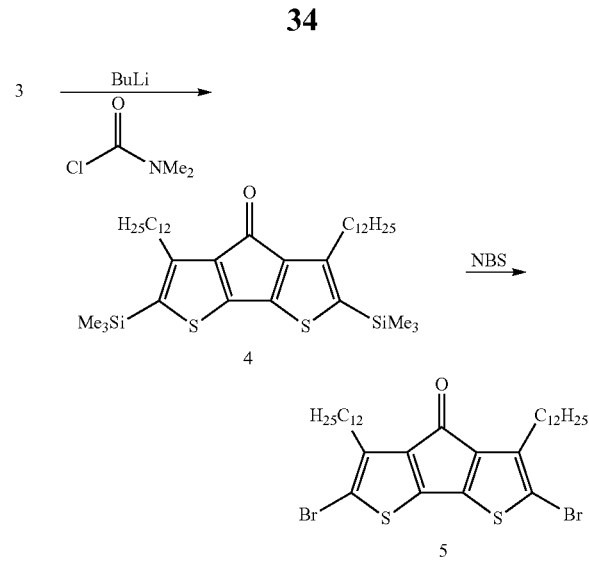

c) Educt 3 is dissolved in 500 ml of dry THF under nitrogen atmosphere and the solution is cooled to −60° C. A 2.7 M solution of BuLi in heptane are added at once and the mixture is allowed to warm to −30° C. followed by addition of 11.5 ml dimethylcarbamyl chloride. After stirring at −20° C. for 15 minutes the mixture is allowed to warm to 0° C. and 100 ml of water are added thereto. The organic phase is separated, washed with brine, dried and evaporated to obtain 4 as a red residue (yield: 58%).

d) For the further reaction to 5, it is not necessary to isolate 4. The organic phase of c) is separated and washed with brine. 37.4 g of N-bromosuccinimide (NBS) are added thereto at 0° C., the mixture is stirred at 0° C. for 30 minutes and at room temperature for an additional hour. After evaporation the residue is washed with water and suspended in 200 ml of methanol. The mixture is heated under reflux for 1 hour and after cooling to room temperature. The product 5 is obtained as dark-violett flakes by filtration (yield: 55%).

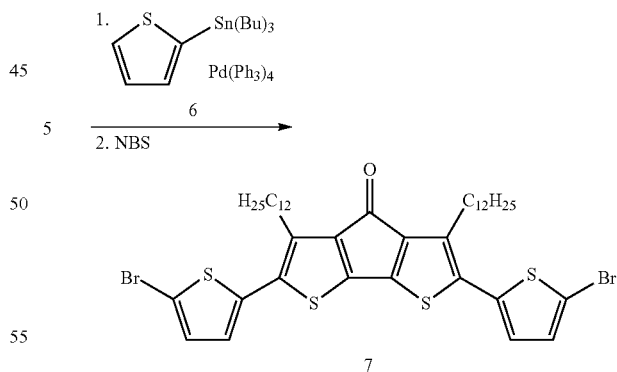

e) 0.94 g of tetrakistriphenylphosphino palladium are added to a degassed solution of 11.13 g of 5 and 15.1 g of 6 in 100 ml of toluene and the mixture is heated under reflux for 16 h, cooled to room temperature and filtered through silica gel. The filtrate is evaporated, the residue is suspended in 100 ml of methanol, stirred for 1 hour and 10.5 g of the 3,5-didodecyl-2,6-di(thien-2-yl)-cyclopenta[2,1-b; 3,4-b']dithiophen-4-one 7 are obtained as dark-bluish solid by filtration (yield: 95%).

11.15 g of the preceding product are dissolved in 100 ml of THF and the solution is cooled to 0° C. 5.7 g NBS are added thereto, and the resulting mixture is stirred at 0° C. for 30 minutes and at room temperature for an additional hour. The solvent is evaporated, the residue is suspended in methanol and 13.0 g of 7 are obtained as dark-bluish solid by filtration (yield: 95%).

Using 4-alkylated 2(tributyltin)-thiophene (with alkyl=n-butyl [7a], 2-ethylhexyl [7b], n-dodecyl [7c]) rather than 6, the corresponding dialkylated variants 7a, 7b or 7c are obtained in an analogous procedure.

f) A further reaction sequence in analogy to the one described under item (e) above and using the reagents identified in the below schemes fi or fii leads to the product 8 or 8':

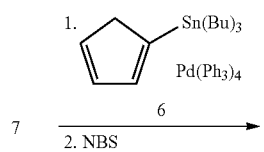

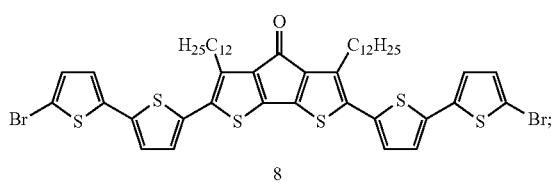

fii:

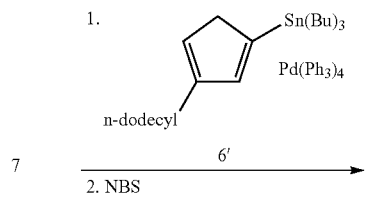

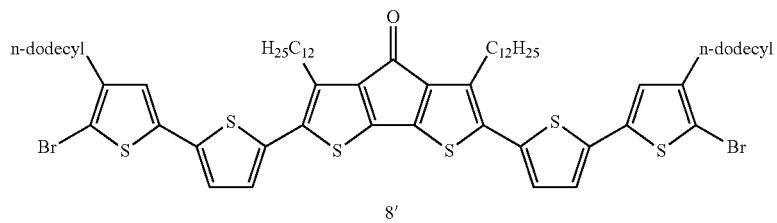

Example 2

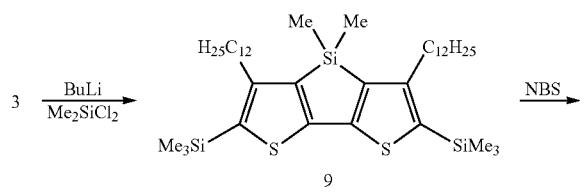

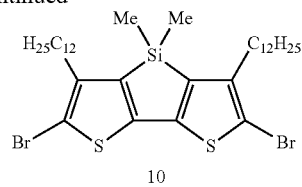

a) A solution of 3 (see example 1b above) in 150 ml of dry THF is cooled to −40° C. 16 ml of a 2.7 M solution of BuLi in heptane are added and the resulting solution is stirred at −20° C. for 15 minutes. 2.58 g of dimethyl dichloro silane are added thereto and the mixture is stirred at 0° C. for 30 minutes and at room temperature for an additional hour followed by adding of 50 ml of 1 N hydrochloric acid. The organic phase is separated, washed with brine, dried and evaporated to obtain 9 as colourless liquid (yield: 95%).

b) Bromination using NBS in analogy to the method shown in example 1e yields 10.

c) The same reaction sequence shown in the above sections (a) and (b), but replacing dimethyl dichloro silane with the equivalent amount of diphenyl dichloro silane, gives 30 in 90% overall yield:

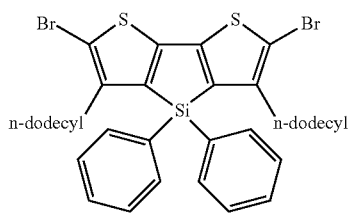

d) The same reaction sequence shown in the above section (a), but starting from 4,4'-di-n-hexyl-3,3',-dibromio-5,5'-di(trimethylsilyl)-2,2-dithiophene 3' rather than from the corresponding 4,4'-n-didodecyl educt 3 yields 38:

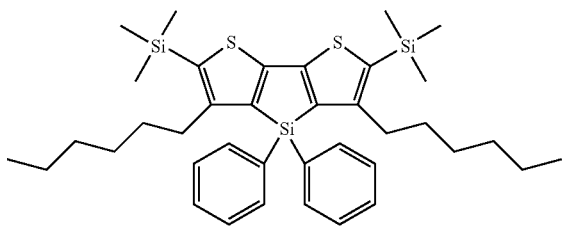

e) The same reaction sequence shown in section (e) of example 1, but starting from the above educt 10 rather than from educt 5, yields 40:

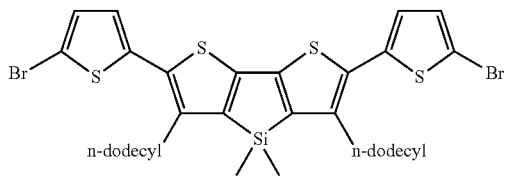

Example 3

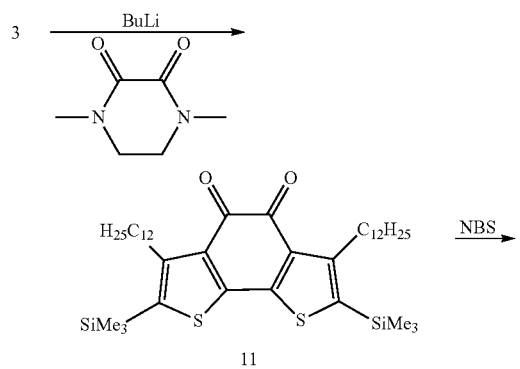

-continued

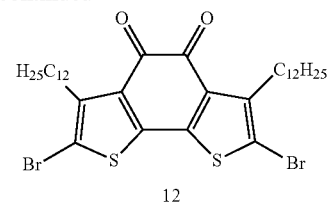

a) 11 is obtained as red powder (yield: 40%) according to example 2a with the exception that 3.20 g of 1,4-dimethylpiperazine-2,3-dione are used instead of dichlorodimethylsilane.

b) Bromination using NBS in analogy to the method shown in example 1e yields 12.

Example 4

3,3'-dibromo-5,5'-di-trimethylsilyl-2,2'-dithiophene

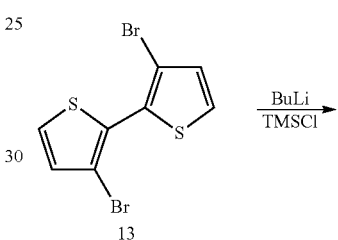

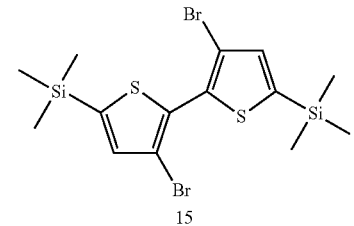

To a freshly prepared LDA solution (82 ml butyllithium [2.7 m in heptane], 22.6 g di-isopropyl amine and 300 ml dry THF) at −78° C. under a nitrogen atmosphere, a solution of 32.4 g 3,3'-dibromo-2,2'-dithiophene 13 in 150 ml of dry THF is slowly added. The solution is slowly warmed to −20° C., stirred for 15 minutes and then re-cooled to −78° C. 27.2 g trimethyl silylchloride is added at once and the solution is slowly allowed to warm to 0° C. After stirring for 1 hour at 0° C. the reaction mixture is quenched by adding 100 ml water. The phases are separated and the organic phase is washed twice with brine and dried over sodium sulphate. The residue is suspended in methanol and the formed solid is recovered by filtration and dried under vacuum. Affords 43 g (92%) of the title compound 15 as an off-white powder.

Example 5

1,6 di-trimethylsilyl-3,4-cyclopentathiophenone and 1,6 dibromo-3,4-cyclopentathiophenone

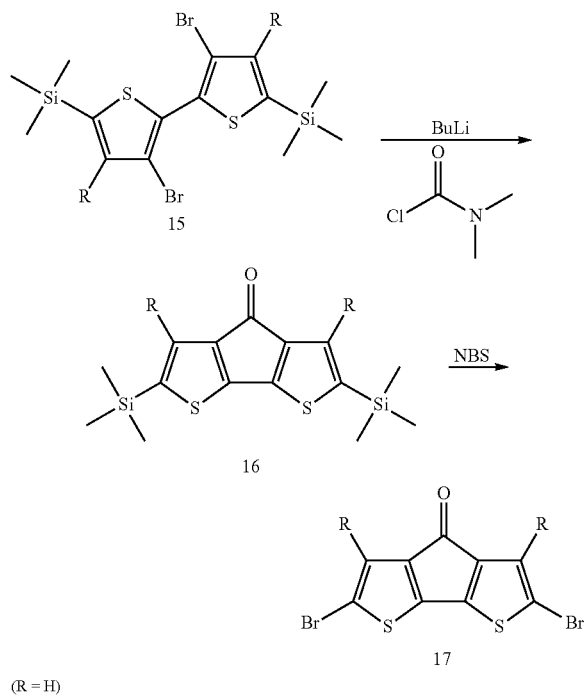

(R = H)

46.8 g 3,3'-dibromo-5,5'-di-trimethylsilyl-2,2'-dithiophene is dissolved in 500 ml of dry THF under a nitrogen atmosphere and cooled to −60° C. 78 ml butyl lithium (2.7 M in heptane) is added at once. The temperature rises to approximately −40° C. The dry ice bath is removed and the reaction mixture is slowly warmed to −30° C. At this point 11.5 ml dimethyl carbamoylchloride in 20 ml dry THF is added at once. The temperature rises to approximately −20° C. and the reaction mixture is stirred at that temperature for 15 minutes and then slowly warmed to 0° C. The reaction mixture is quenched by adding 100 ml water. The phases are separated and the organic phase is washed twice with brine and dried over sodium sulphate. Evaporation of the solvent affords 33.1 g of a red residue, which contains approximately 90% product 16 (NMR; corresponds to 88.5% yield). Purification can be achieved either by flash chromatography or suspension in methanol.

1,6 dibromo-3,4-cyclopentathiophenone 17: The reaction mixture is quenched by adding 100 ml water. The phases are separated and the organic phase is once washed with brine. After phase separation 37.4 g N-bromo succinimide are added to the organic ohase at once at 0° C. The reaction mixture is stirred for 30 minutes at 0° C. and 1 hour at room temperature. After evaporation to dryness the residue is washed twice with 200 ml water each, which is decanted, and then boiled for 1 hour in 200 ml methanol. After cooling to room temperature the product is collected by filtration. Affords 30.1 g (85.2%) of the title compound 17 as dark-violet flakes.

Example 6

1,6 dibromo-3,4-cyclopentathiophenone Oxime

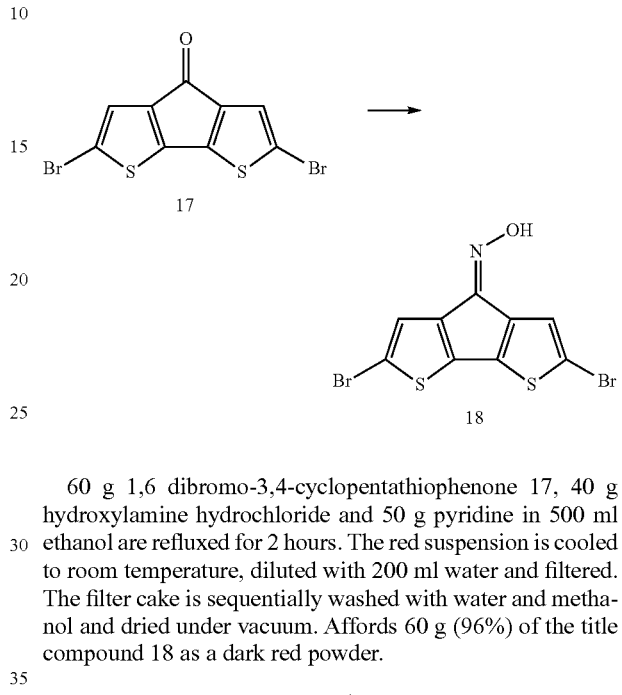

60 g 1,6 dibromo-3,4-cyclopentathiophenone 17, 40 g hydroxylamine hydrochloride and 50 g pyridine in 500 ml ethanol are refluxed for 2 hours. The red suspension is cooled to room temperature, diluted with 200 ml water and filtered. The filter cake is sequentially washed with water and methanol and dried under vacuum. Affords 60 g (96%) of the title compound 18 as a dark red powder.

Example 7

7,7-Dimethyl-2,5-bis-trimethylsilanyl-7H-3,4-dithia-7-sila-cyclopenta[a]pentalene

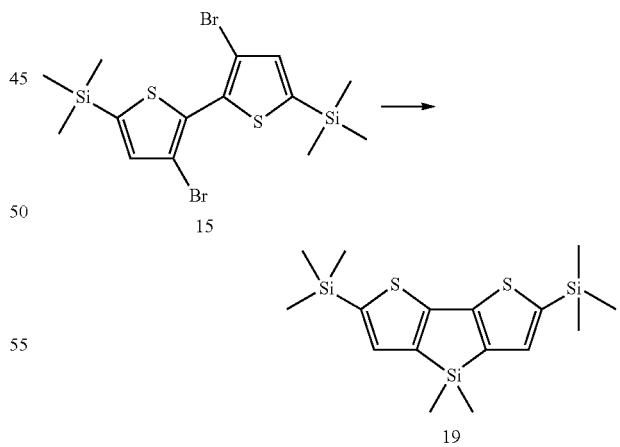

A solution of 9.37 g 3,3'-dibromo-5,5'-di-trimethylsilyl-2,2'-dithiophene in 150 ml dry THF is cooled to −40° C. 16 ml butyl lithium (2.7 M in heptane) are added at once and the resulting solution is stirred for 15 minutes at −20° C. 2.58 g dimethyl dichloro silane are added at once and the reaction mass is stirred for 30 minutes at 0° C. and 1 hour at room temperature. The reaction mixture is quenched by adding 50 ml 1 N HCl. The phases are separated and the organic phase is washed twice with brine and dried over sodium sulphate. Evaporation of the solvent affords 6.95 g (95% of th.) of the title compound as colourless liquid, which is almost pure as determined by NMR.

The same reaction sequence with dimethyl germanium dichloride gives Y in 75% overall yield:

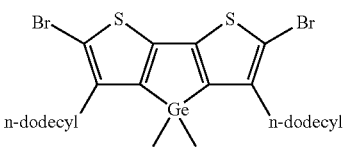

31

Example 8

2,7-Bis-trimethylsilanyl-benzo[2,1-b; 3,4-b']dithiophene-4,5-dione and derivatives a)

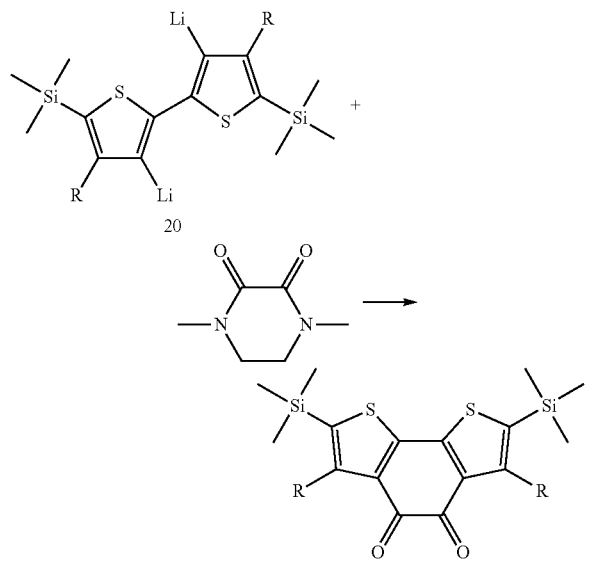

(R = H)

A solution of 9.37 g 3,3'-dibromo-5,5'-di-trimethylsilyl-2,2'-dithiophene in 150 ml dry THF is cooled to −40° C. 16 ml butyl lithium (2.7 M in heptane) are added at once and the resulting solution is stirred for 15 minutes at −20° C. 3.20 g of 1,4-Dimethyl-piperazine-2,3-dione are added in one portion and the reaction mixture is allowed to warm to room temperature and stirred for an additional hour at this temperature. The reaction mixture is quenched by adding 50 ml 1 N HCl. The phases are separated and the organic phase is washed twice with brine and dried over sodium sulphate. Evaporation of the solvent affords a red residue, which is suspended in hexane. The obtained slurry is stirred for 1 hour and then filtered. The filter cake is washed with hexane and dried under vacuum. Affords 3.4 g (46% of th.) of the title compound as a dark red powder.

b) By reacting the above product 21 of example 8a with o-diaminobenzene, the following compound 22 is obtained; using 1,2-diamino-4,5-di(2-ethylhexyloxy)-benzene instead of o-diaminobenzene yields 22b. General procedure: 10 mmol 21 and 10 mmol of the aromatic ortho-diamine are dissolved in 50 ml of ethanol and refluxed for 2 hours. After cooling to 0° C. the yellow precipitate is filtered and washed with cold ethanol and dried in a vacuum oven affording the corresponding quinoxaline 22 or 22b.

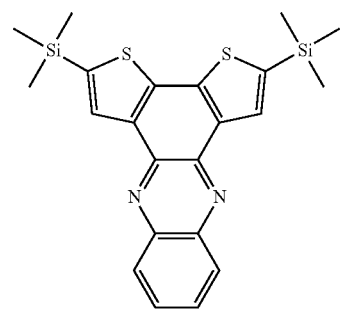

22

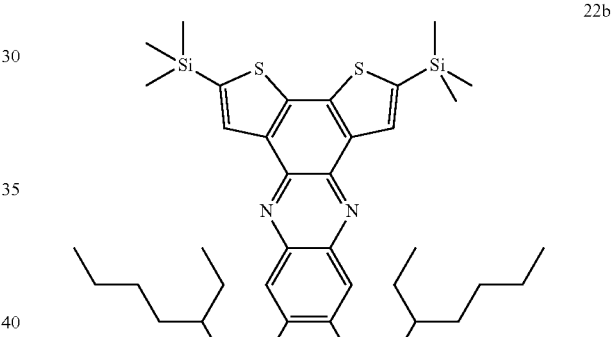

22b

Bromination

To a solution of 22 or 22b in 100 ml THF, 2 equivalents of N-bromo-succinimide are added in one portion and the reaction mixture is heated to 40° C. and stirred at this temperature for 16 hours. The solvent is then evaporated and residue is washed several times with water and then recrystallized from ethanol. The corresponding quinoxaline 22a or 22c (R═Br) in 60-80% yield.

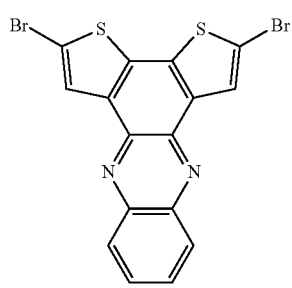

22a

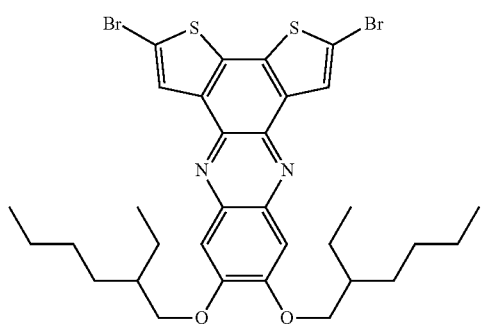

Example 8c

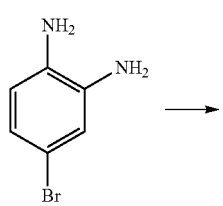

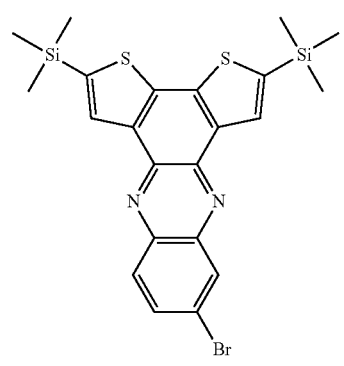

1.82 g (5 mmol) of 21 and 0.94 g (5 mmol) of 2-amino-4-bromoaniline is refluxed overnight in 10 ml Ethanol, cooled down to RT and product is filtered off. Yield 2.4 g (93%) of product 38.

d)

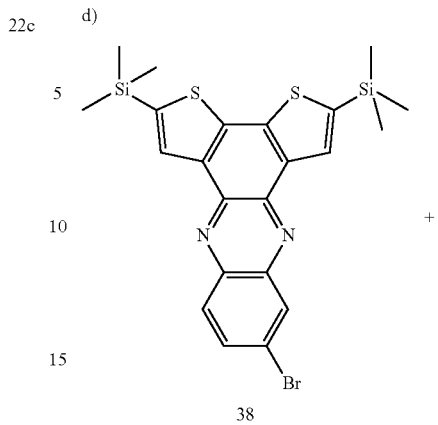

2.4 g (4.65 mmol) of product 38, 0.93 g (6.97 mmol) potassium vinyltrifluoroborate, 0.42 g (0.465 mmol) tris(dibenzylideneacetone)dipalladium(0), 6.7 g (23.25 mmol) tri-t-butylphosphonium tetrafluoroborate are mixed in 20 ml THF, degassed and heated to 50° C. Degassed aqueous solution of potassium phosphate is added and reaction mixture is stirred at reflux for 3 h. Product is purified by column chromatography with hexane:ethyl acetate (1:20). Yield 1.3 g (59.1%) of product 39.

Example 9

Polymer of 3,5-Didodecyl-2,6-di-(5-bromo)thiophen-2-yl-cyclopenta[2,1-b; 3,4-b']dithiophen-4-one (Yamamoto Polymerization)

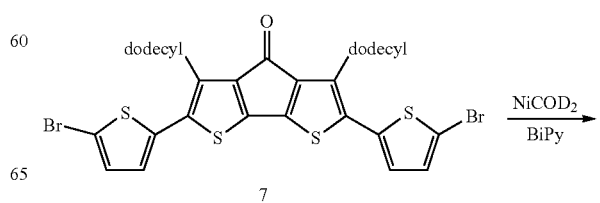

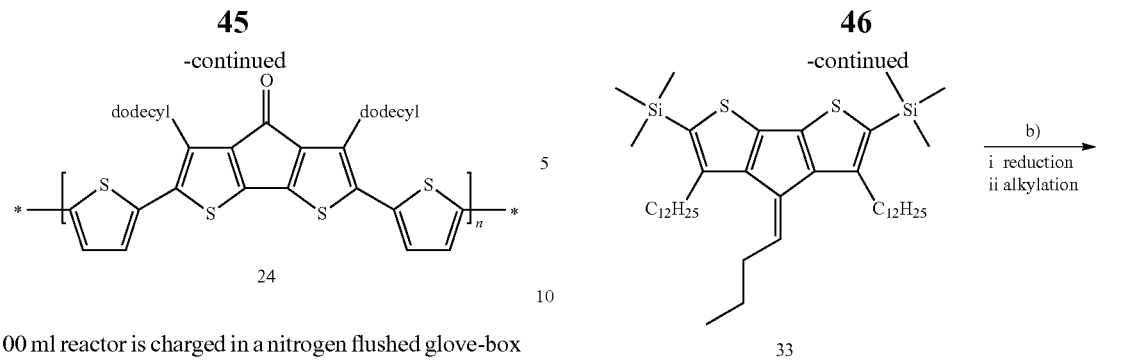

A 100 ml reactor is charged in a nitrogen flushed glove-box with 1.48 g NiCOD$_2$ and 0.84 g 2,2'-bipyridine. After the addition of 20 ml toluene (degassed) the reactor is sealed with a septum and the reaction mixture is homogenized in an ultra sound bath until a deep-blue slurry is obtained. 3 g 3,5-Didodecyl-2,6-di-(5-bromo)thiophen-2-yl-cyclopenta[2,1-b;3,4-b']dithiophen-4-one are dissolved in 15 ml toluene and degas-sed. This solution is added via a syringe to the nickel solution from above and the whole mixture is heated to 80° C. After 30 minutes, the product is isolated as a solid, rubber-like dark-blue mass.

Using the tetraalkylated starting materials 7a, 7b or 7c, polymers 23, 25 and 26 of structure analogous to 24, but containing 4 alkyl groups in each monomer unit, are obtained.

Example 10

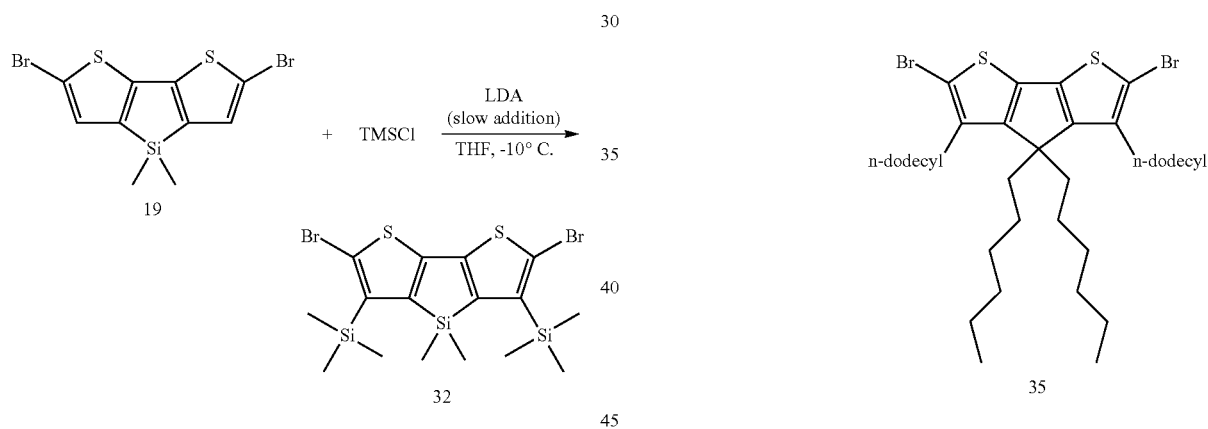

5 g 19 and 5 eq. trimethyl chloro silane are dissolved in 50 ml THF and cooled to −10° C. A freshly prepared LDA-solution (from 2.1 eq. butyl lithium and 2.2 eq. diisopropyl amine in 20 ml THF) is slowly dropped to the solution above. The solution is stirred for 1 hour at −10° C. and then slowly warmed to 0° C. The reaction is quenched by the addition of saturated NH$_4$Cl-solution. Work-up gives 32 in 90% yield.

Example 11

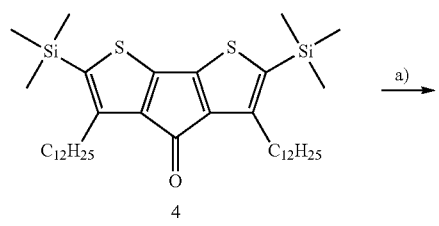

a) A solution of 0.5 g 4 in 5 ml THF is treated at −20° C. with 1.1 eq. butyl lithium and then slowly warmed to 0° C. The reaction is quenched by the addition of 1.1 eq. trifluoro acetic anhydride and stirred for an additional hour at room temperature.

10 ml tert.butylmethylether are added the reaction mixture is washed with sodium bicarbonate and brine. The organic phase is separated and dried over sodium sulphate and evaporated to dryness. The residue is dissolved in 5 ml DMSO and 0.1 ml trifluoroacetic acid and stirred for 5 hours at 70° C., cooled down and poured onto a saturated sodium bicarbonate solution. The aqueous slurry is extracted twice with tert.butyl-methylether, the combined organic phases are washed with brine, dried over sodium sulphate and evaporated to dryness. Afford 0.35 g 33 as a greyish-white solid.

b) A solution of the product from above in toluene is treated with 3 eq. Red-Al (1 M in THF) and stirred at 80° C. for 2 hours. After cooling down the reaction mixture is subsequently washed with diluted HCl and brine. The organic phase is dried over sodium sulphate and evaporated to dryness.

The residue from above is dissolved in DMSO and, after the addition of 1.5 eq. butyl bromide, 5 eq. KOH and a catalytical amount of KI, stirred for 16 hours at room temperature. The reaction mass is poured onto diluted HCl and the aqueous slurry is extracted twice with hexane. The combined organic phases are washed with brine, dried over sodium sulphate and evaporated to dryness. The residue is further purified by flash chromatography affording 0.29 g 34 as a white solid.

c) Bromination according to the method described in the last step of example 8 yields 35.

Example 12

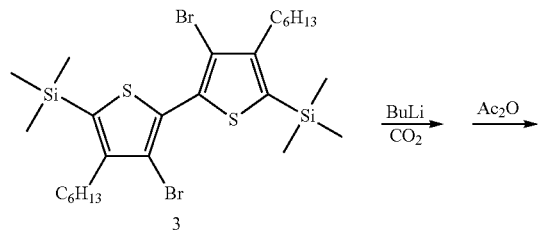

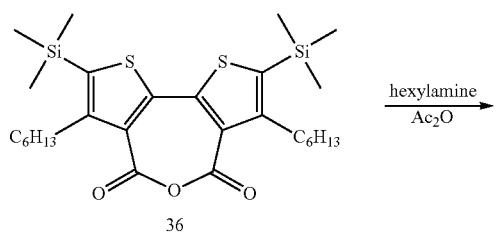

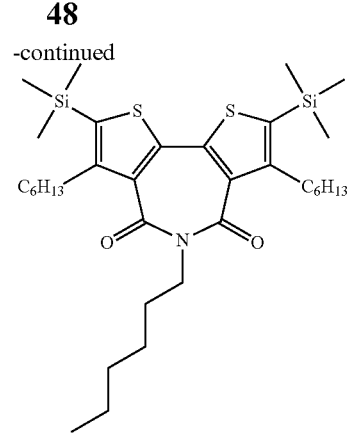

a) 10 g 3 are lithiated as described in Ex.1 c) and then cooled to −78° C. 5 g solid carbon dioxide is added in one portion and the solution is allowed to warm to room temperature. The solution is again cooled to 0° C., quenched with diluted HCl and twice extracted with TBME. The combined organic phases are washed with brine, dried over sodium sulphate and evaporated to dryness. 50 ml acetic anhydride is added to the residue and the suspension is refluxed for 2 hours. After cooling down the slurry is extracted several times with hexane, the combined hexane phases are evaporated to dryness and further dried in a vacuum oven affording 7.4 g 36 as a reddish-white solid.

b) The product from above is dissolved in THF, treated at 0° C. with 2.2 eq. hexylamine and stirred for 1 hour at room temperature. After standard work-up (TBME, diluted HCl, brine) the residue is suspended in acetic acid, treated with 10 eq. each of acetic anhydride and sodium acetate and refluxed for 16 hours. Then most of the solvent is evaporated and the residue is suspended in aqueous sodium bicarbonate, followed by extraction with TBME. The combined organic layers are washed with brine, dried and evaporated dryness affording 7.6 g 37 as a yellowish solid.

Physical Data of a number of compounds prepared are compiled in the following table:

| No | Structure | NMR |
|---|---|---|
| 15 | (Br, Br substituted bis-trimethylsilyl bithiophene) | $^1H$NMR: δ (ppm) 0.00 (s, 18 H), 6.81 (s, 2 H)<br>$^{13}C$NMR: δ (ppm) 0.00 (TMS), 113.14 (C3), 134.11, 137.15, 143.05 |
| 16 | (bis-trimethylsilyl cyclopentadithiophenone) | $^1H$NMR: δ (ppm) 7.05 (s, 2H)<br>$^{13}C$NMR: δ (ppm) 125.41 (C4), 141.08 (C2), 147.42 (C3), 152.21 (C5), 180.51 (C=O) |
| 17 | (dibromo cyclopentadithiophenone) | $^1H$NMR: δ (ppm) 6.99 (s, 2H)<br>$^{13}C$NMR: δ (ppm) 114.17 (C5), 124.62 (C4), 139.74 (C2), 148.80 (C3), 180.51 (C=O) |

-continued

| No | Structure | NMR |
|---|---|---|
| 1 | 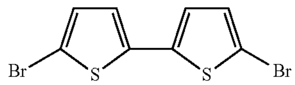 [SMILES: Brc1ccc(-c2ccc(Br)s2)s1] | $^{1H}$NMR: δ (ppm)<br>$^{13C}$NMR: δ (ppm) |
|  | | $^{1H}$NMR: δ (ppm)<br>$^{13C}$NMR: δ (ppm) |
| 2 | 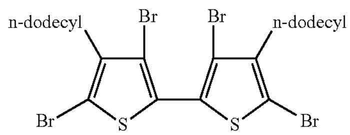 | $^{1H}$NMR: δ (ppm) 0.89 (t, 6H), 1.27 (m, 36 H (18xCH$_2$)), 1.56 (m, 4H), 2.67 (dd, 4H)<br>$^{13C}$NMR: δ (ppm) 14.51 (CH$_3$), 23.08 (CH2), 28.93-32.31 (9xCH$_2$), 111.28 (C5), 114.82 (C3), 128.80 (C4), 141.68 (C2) |
| 3 | 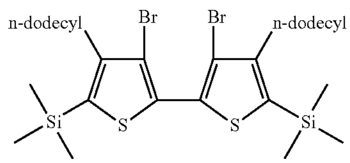 | $^{1H}$NMR: δ (ppm)<br>$^{13C}$NMR: δ (ppm) |
| 4 | 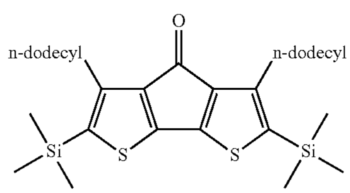 | $^{1H}$NMR: δ (ppm) 0.35 (s, 18 H), 0.90 (t, 6H), 1.28 (m, 36 H (18xCH$_2$)), 1.61 (m, 4H), 2.69 (dd, 4H)<br>$^{13C}$NMR: δ (ppm) 0.00 (TMS), 13.72 (CH$_3$), 22.23 (CH2), 28.95-31.52 (9xCH$_2$), 136.45, 142.98, 146.82, 152.40, 183.66 |
| 5 | 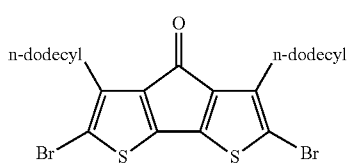 | $^{1H}$NMR: δ (ppm) 0.88 (t, 6H), 1.26 (m. 36 H (18xCH$_2$)), 1.59 (m. 4H), 2.57 (dd, 4H)<br>$^{13C}$NMR: δ (ppm) 14.50 (CH$_3$), 23.09 (CH2). 29.40-32.31 (9xCH$_2$), 111.10 (C-Br), 137.31, 139.78, 147.35, 182.13 |
|  | | $^{1H}$NMR: δ (ppm) 0.93 (t, 6H), 1.32 (m, 36 H (18xCH$_2$)), 1.65 (m, 4H), 2.83 (dd. 4H). 7.06 (m, 2H), 7.10 (m. 2H), 7.32 (dd, 2H)<br>$^{13C}$NMR: δ (ppm) 14.51 (CH$_3$), 23.08 (CH2), 28.60-32.31 (9xCH$_2$), 126.02, 126.32, 127.68, 134.15, 135.32, 141.04, 146.84, 184.20 (C=O) |
| 7c | 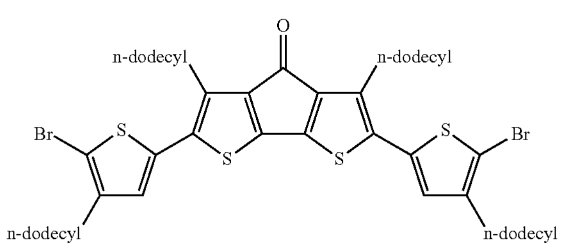 | $^{1H}$NMR: δ (ppm) 0.85 (2xt, 12H), 1.1-1.4 (m, 40 H), 1.59 (m, 8H), 2.48 (dd, 8H), 7.77 (s, 2H) |
| 21 | 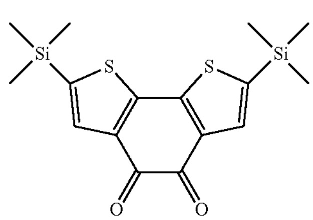 | $^{1H}$NMR: δ (ppm) 0.00 (s, 18H), 7.23 (s, 2H)<br>$^{13C}$NMR: δ (ppm) 0.00, 134.53, 136.08, 142.68, 148.47, 175.31 |

| No | Structure | NMR |
|---|---|---|
| 22 | 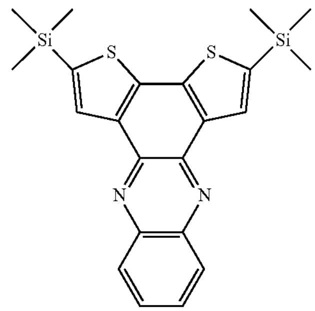 | $^{1H}$NMR: δ (ppm) 0.20 (s, 18H), 7.47 (dd, 2H), 7.94 (dd, 2H), 8.17 (s, 2H)<br>$^{13C}$NMR: δ (ppm) 0.00, 129.08, 131.48, 135.64, 139.82, 140.01, 140.45, 141.26 |
| 22c | 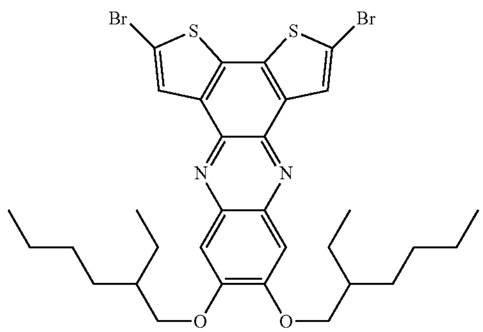 [SMILES: CCCCC(CC)COc1cc2nc3c4cc(Br)sc4c4sc(Br)cc4c3nc2cc1OCC(CC)CCCC] | $^{1H}$NMR: δ (ppm) 0.98 (t, 6H), 1.06 (t, 6H), 1.42 (m, 8H), 1.62 (m, 8H), 1.96 (m, 2H), 4.13 (d, 4H), 7.19 (s, 2H), 7.97 (s, 2H)<br>$^{13C}$NMR: δ (ppm) 23.15, 24.09, 24.12, 29.18, 30.73, 30.74, 39.34, 71.58, 105.65, 112.51, 126.93, 133.24, 134.48, 135.53, 139.87, 154.10 |
| 19 | 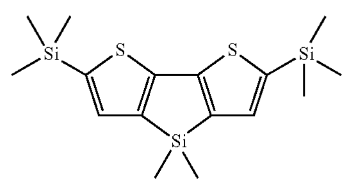 | $^{1H}$NMR: δ (ppm) 0.00 (s, 18H), 0.08 (s, 6H), 6.83 (s, 2 H) |
| 10 | 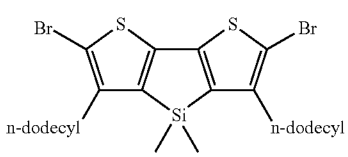 | $^{13C}$NMR: δ (ppm) 0.02, 17.30, 25.89, 31-38 (tot. 20 C), 111.186, 144.48, 147.95, 150.01 |
| 11 | 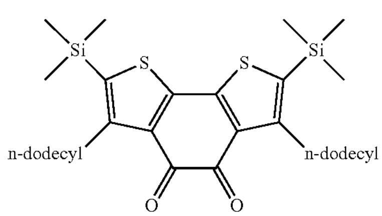 | $^{1H}$NMR: δ (ppm) 0.00 (s, 18H), 0.87 (t, 6H), 1.24 (m, 36 H (18xCH$_2$)), 1.62 (m, 4H), 2.57 (dd, 4H)<br>$^{13C}$NMR: δ (ppm) 0.00 (TMS), 13.79 (CH$_3$), 21.97 (CH2), 28.63-31.72 (10xCH$_2$), 136.45, 142.98, 146.82, 152.40, 174.83 |
| 32 | 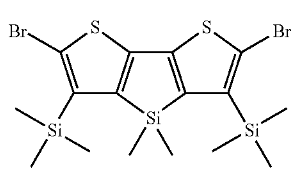 | $^{1H}$NMR: δ (ppm) 0.42 (s, 18H), 0.53 (s, 6H) |

-continued

| No | Structure | NMR |
|---|---|---|
| 35 | 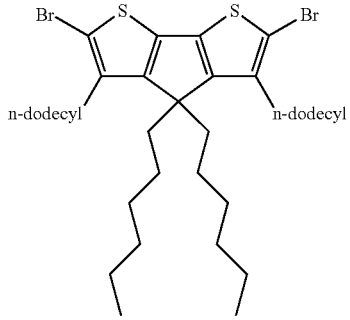 n-dodecyl, n-dodecyl | $^{1H}$NMR: δ (ppm) 0.81 (2x t, 12H), 0.9 (m, 4H), 1.1-1.3 (m, 46H), 1.48 (m, 4H), 1.78 (m, 4H), 2.63 (dd, 4H) |
| 36 | 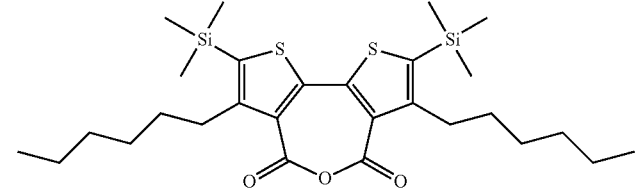 [SMILES: CCCCCCc1c([Si](C)(C)C)sc2c1c(=O)oc(=O)c1c(CCCCCC)c([Si](C)(C)C)sc12] | $^{1H}$NMR: δ (ppm) 0.32 (s, 18 H), 0.84 (t, 6H), 1.1-1.4 (m, 12H), 1.48 (m, 4H), 2.45 (dd, 4H) |
| 37 | 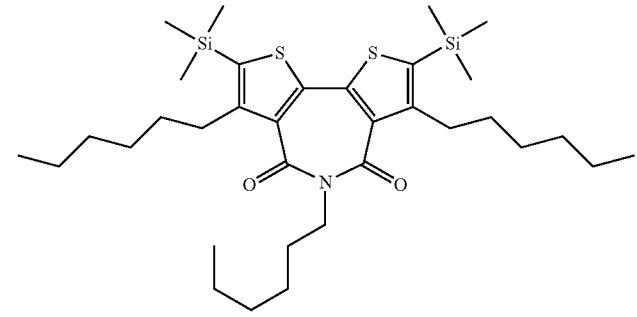 [SMILES: CCCCCCc1c([Si](C)(C)C)sc2c1c(=O)n(CCCCCC)c(=O)c1c(CCCCCC)c([Si](C)(C)C)sc12] | $^{1H}$NMR: δ (ppm) 0.00 (s, 18 H), 0.54 (t, 6H), 0.59 (t, 3H), 1.0-1.3 (m. 18H), 1.40 (m. 6H), 2.45 (dd, 4H). 3.81 (dd, 2H) |
| 38 | 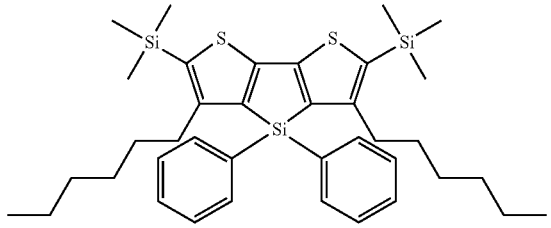 [SMILES: CCCCCCc1c([Si](C)(C)C)sc2c1[Si](c1ccccc1)(c1ccccc1)c1c-2sc([Si](C)(C)C)c1CCCCCC] | $^{1H}$NMR: δ (ppm) 0.34 (s, 18 H), 0.87 (t, 6H), 1.1-1.4 (m, 16H), 2.41 (dd, 4H), 7.3-7.4 (m, 8H), 7.65 (m, 2H)<br>$^{13C}$NMR: δ (ppm) 0.00, 14.72, 23.15, 28.72, 29.31, 29.89, 31.56, 129.84, 135.02, 136.01, 141.08, 141.41, 155.18 |
| 40 | 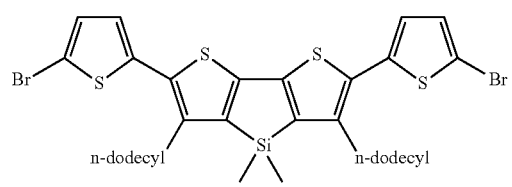 n-dodecyl, n-dodecyl | $^{1H}$NMR: δ (ppm) 0.40 (s, 6H), 0.78 (t, 6H), 1.1-1.3 (m, 36H), 1.45 (m, 4H), 2.61 (dd, 4H), 6.73 (d, 2H), 6.87 (d, 2H)<br>$^{13C}$NMR: δ (ppm) 0.00, 17.20, 25.77, 31-38 (tot. 20 C), 114.40, 127.95, 133.05, 133.50, 140.71, 147.83, 148.19, 149.58 |

Application Examples

Field-Effect Transistors a) Experimental

Bottom-gate thin-film transistor (TFT) structures with p-Si gate are used for all experiments. A high-quality thermal SiO2 layer serves as gate-insulator of $C_i$=32.6 nF/cm2 capacitance per unit area. Source and drain electrodes are patterned by photolithography directly on the gate-oxide (bottom-contact configuration). On each substrate 16 transistors are present with Au source/drain electrodes defining channels of different length. Prior to the deposition of the organic semiconductor, the SiO2 surface is derivatized with hexamethyldisilazane (HMDS) or octadecyltrichlorosilane (OTS). The films are prepared either by spin casting or drop casting the polymer obtained in example w), x), y) in different solvents. The transistor behaviour is measured on an automated tester elaborated by CSEM, Transistor Prober TP-10.

b) Transistor Performance

The thin-film transistors prepared using the compound 24 of example 9 show p-type transistor behavior. The transistors show a good field effect mobility and threshold voltage. The transistors show on/off current ratios of $10^3$.

Good results are also obtained with thin-film transistors prepared using the polymer 23, 25 or 26.

The invention claimed is:

1. A process for the preparation of a substituted 2,2'-dithiophene, which process comprises the steps a) reaction of a compound of the formula (IV)

wherein Hal stands for hydrogen or halogen,

R1 and R1' independently are hydrogen or a substituent, n ranges from 0 to 6;

Y, if present, is substituted or unsubstituted phenylene, thiene, 1,2-ethylene, or is 1,2-ethinylene;

R2 and R2' independently are hydrogen or are selected from $C_1$-$C_{25}$alkyl, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted, and R2 and/or R2' may also be halogen;

with a lithium organic compound;

b) optional exchange of lithium against another metal selected from Mg, Zn and Cu by reaction with a metal salt or metal organic compound; followed by c) reaction of the metallated intermediate obtained in step (a) or (b) with an electrophile, which is $CO_2$, an aldehyde (addition reaction), a compound Y'—R17 or Y'—R18-Z (substitution reaction), where R17 is an acyl or silyl residue, R18 is selected from CO, CO—CO, where R4, R5, and R10 are selected from $C_1$-$C_{25}$alkyl, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;

Y' and Z' are suitable leaving groups allowing for a reaction with the metal thienyl intermediate formed in step (a) or (b); and optionally d) modification of the product obtained in step (c), by introducing one or more conjugating moieties Y as defined above, ring closure between monovalent residues R17, exchange or extension of functional groups or substituents in R17 or R18.

2. Process of claim 1 for the preparation of a substituted 2,2'-dithiophene, which conforms to the formula (XI)

(XII)

wherein $R^1$ and $R^{1'}$ independently of each other are H or a substituent, halogen or, in case that n is not 0, may be $SiR^6R^4R^5$;

$R^2$ and $R^{2'}$ may be the same or different and are selected from $C_1$-$C_{25}$alkyl, $C_3$-$C_{12}$cycloalkyl, $C_2$-$C_{25}$alkenyl, $C_2$-$C_{25}$alkynyl, $C_4$-$C_{25}$aryl, $C_5$-$C_{25}$alkylaryl or $C_5$-$C_{25}$aralkyl, each of which is unsubstituted or substituted, and R2 and/or R2' may also be halogen; and in case that R3 and R3', or R7 and R7', together are the bridging group $R^2$ and $R^{2'}$ independently may also be hydrogen;

R4, R5, R6, R4', R5', R6' independently are selected from $C_1$-$C_{25}$alkyl, $C_3$-$C_{12}$cycloalkyl, $C_4$-$C_{25}$aryl, or $C_5$-$C_{25}$aralkyl; and the neighbouring residues R4 and R5, and correspondingly R4' and R5', may further be interlinked to form a divalent hydrocarbon residue of 4 to 25 carbon atoms which may be substituted and/or interrupted;

R3 and R3', independently, are as defined for R7, R7';

R7, R7' independently are $C_1$-$C_{25}$alkyl, $C_2$-$C_{25}$alkenyl, $C_2$-$C_{25}$alkynyl, $C_1$-$C_{25}$acyl, $C_2$-$C_{25}$alkoxycarbonyl, $C_1$-$C_{25}$acyloxy, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted; or R7 and R7', together are a bridging group selected from

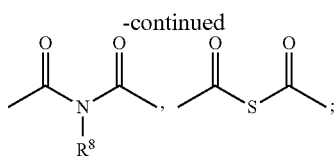

and R3 and R3' together, may also form a bridging group

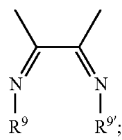

M is Si or Ge;
Y is selected from

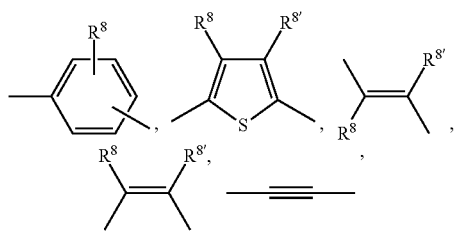

n ranges from 0 to 6;
R8 and R8' independently are H or a substituent;
R9 and R9' together form a bridging group selected from

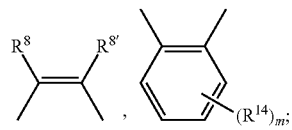

R10 is $C_1$-$C_{25}$alkyl, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;
R11 is as defined for R8 or is OR8;
one of R12 and R13 may be hydrogen while the other, or both R12 and R13, are substituents; or both R12 and R13 are interlinked to form a divalent hydrocarbon residue of 2 to 25 carbon atoms which may be substituted and/or interrupted;
m is 0, 1, 2, 3 or 4, and R14 is a substituent, or 2 or 3 neighbouring residues R14 may be interlinked to form a divalent or trivalent hydrocarbon residue of 4 to 25 carbon atoms which may be substituted and/or interrupted; and
any substituent, if present, is selected from halogen, OR, $C_1$-$C_{25}$alkyl, $C_2$-$C_{25}$alkenyl, $C_1$-$C_{25}$alkylthio, $C_1$-$C_{25}$acyl, $C_4$-$C_{10}$aryl, $C_1$-$C_9$heteroaryl, $C_3$-$C_{12}$cycloalkyl, heterocycloalkyl, $C_1$-$C_{25}$acyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R'', PORR', PO(OR)R', PO(OR)$_2$, PO(NHR)$_2$, PO(NRR')$_2$, CN, $NO_2$, NHR, NRR', NH—NHR, NH—NRR', CONROH;
where R, R' and R'' independently are selected from $C_1$-$C_{25}$alkyl, $C_1$-$C_{25}$haloalkyl, $C_5$-$C_{10}$aryl, $C_3$-$C_{12}$cycloalkyl;
and R may also be hydrogen.

3. Process according to claim 1, wherein the intermediate obtained in step (a) or (b) is reacted in step (c) with

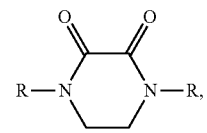

wherein R independently is selected from hydrogen, $C_1$-$C_{18}$alkyl, $C_1$-$C_{18}$haloalkyl, $C_5$-$C_{10}$aryl, $C_3$-$C_{12}$cycloalkyl, to obtain a compound of the formula

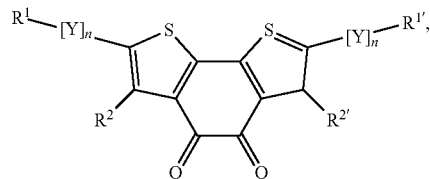

which is optionally further modified in step (d).

4. A compound of the formula

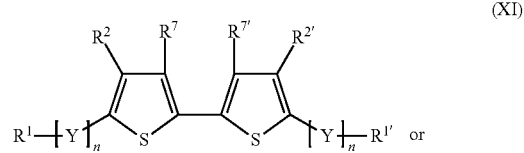

(XI)

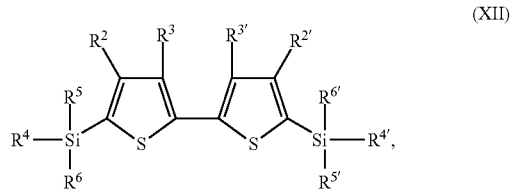

(XII)

wherein
$R^1$ and $R^{1'}$ independently of each other are H or a substituent, halogen or, in case that n is not 0, may be $SiR^6R^4R^5$;
$R^2$ and $R^{2'}$ may be the same or different and are selected from $C_1$-$C_{25}$alkyl, $C_3$-$C_{12}$cycloalkyl, $C_2$-$C_{25}$alkenyl, $C_2$-$C_{25}$alkynyl, $C_4$-$C_{25}$aryl, $C_5$-$C_{25}$alkylaryl or $C_5$-$C_{25}$aralkyl, each of which is unsubstituted or substituted, and R2 and/or R2' may also be halogen; and in case that R3 and R3', or R7 and R7', together are the bridging group

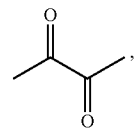

$R^2$ and $R^{2'}$ independently may also be hydrogen;

R4, R5, R6, R4', R5', R6' independently are selected from $C_1$-$C_{25}$alkyl, $C_3$-$C_{12}$cycloalkyl, $C_4$-$C_{25}$aryl, or $C_5$-$C_{25}$aralkyl; and the neighbouring residues R4 and R5, and correspondingly R4' and R5', may further be interlinked to form a divalent hydrocarbon residue of 4 to 25 carbon atoms which may be substituted and/or interrupted;

R3 and R3', independently, are as defined for R7, R7';

R7, R7' independently are $C_1$-$C_{25}$alkyl, $C_2$-$C_{25}$alkenyl, $C_2$-$C_{25}$alkynyl, $C_2$-$C_{25}$alkoxycarbonyl, $C_1$-$C_{25}$acyl, $C_1$-$C_{25}$acyloxy, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;

or R7 and R7', together are a bridging group selected from

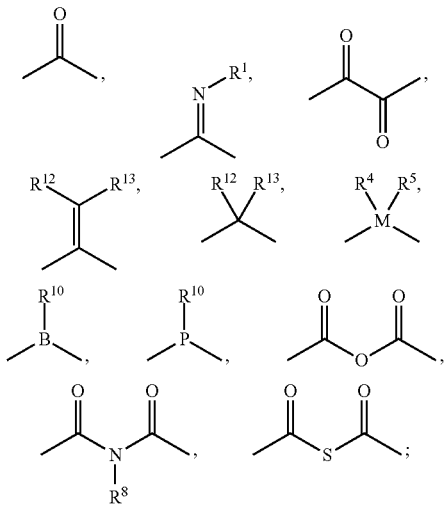

and R3 and R3' together, may also form a bridging group

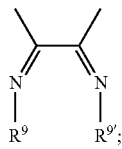

M is Si or Ge;
Y is selected from

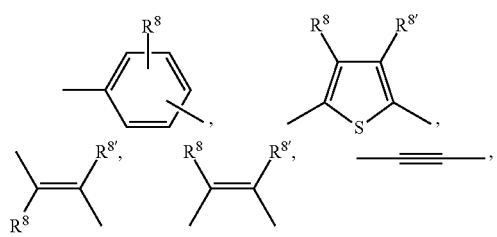

n ranges from 0 to 6;
R8 and R8' independently are H or a substituent;

R9 and R9' together form a bridging group selected from

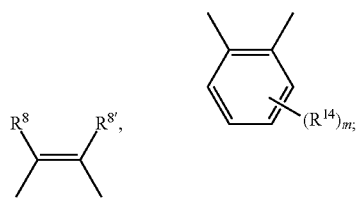

R10 is $C_1$-$C_{25}$alkyl, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;

R11 is as defined for R8 or is OR8;

one of R12 and R13 may be hydrogen while the other, or both R12 and R13, are substituents; or both R12 and R13 are interlinked to form a divalent hydrocarbon residue of 2 to 25 carbon atoms which may be substituted and/or interrupted;

m is 0, 1, 2, 3 or 4, and R14 is a substituent, or 2 or 3 neighbouring residues R14 may be interlinked to form a divalent or trivalent hydrocarbon residue of 4 to 25 carbon atoms which may be substituted and/or interrupted;

and any substituent, if present, is selected from halogen, OR, $C_1$-$C_{25}$alkyl, $C_2$-$C_{25}$alkenyl, $C_1$-$C_{25}$alkylthio, $C_1$-$C_{25}$acyl, $C_4$-$C_{10}$aryl, $C_1$-$C_9$heteroaryl, $C_3$-$C_{12}$cycloalkyl, $C_2$-$C_{11}$ heterocycloalkyl, $C_1$-$C_{25}$acyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R", PORR', PO(OR)R', $PO(OR)_2$, $PO(NHR)_2$, $PO(NRR')_2$, CN, $NO_2$, NHR, NRR', NH—NHR, NH—NRR', CONROH;

where R, R' and R" independently are selected from $C_1$-$C_{25}$alkyl, $C_1$-$C_{25}$haloalkyl, $C_5$-$C_{10}$aryl, $C_3$-$C_{12}$cycloalkyl;

and R may also be hydrogen;

provided that if R7 and R7' together are —CO—, at least one of R2 and R2' contains at least 2 carbon atoms.

5. Compound of claim 4, which conforms to the formula

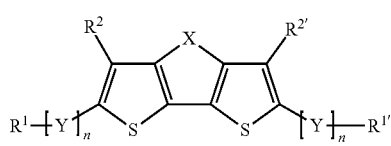

(X)

wherein $R^1$ and $R^{1'}$ are independently of each other H, halogen or $SiR^6R^4R^5$;

$R^2$ and $R^{2'}$ may be the same or different and are selected from $C_4$-$C_{25}$alkyl, $C_2$-$C_{25}$alkenyl, $C_2$-$C_{25}$alkynyl, $C_5$-$C_{12}$cycloalkyl, $C_4$-$C_{25}$aryl, $C_5$-$C_{25}$alkylaryl or $C_5$-$C_{25}$aralkyl, each of which is unsubstituted or substituted, and R2 and/or R2' may also be halogen; and in case that $R^1$ or $R^{1'}$ is $SiR^6R^4R^5$, and/or X is the bridging group

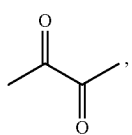

$R^2$ and $R^{2'}$ independently may also be hydrogen or $C_1$-$C_3$alkyl;

R4, R5, R6, R4', R5', R6' independently are selected from $C_1$-$C_{12}$alkyl, $C_5$-$C_{12}$cycloalkyl, phenyl, or $C_7$-$C_{12}$phenylalkyl;

X is a bridging group selected from

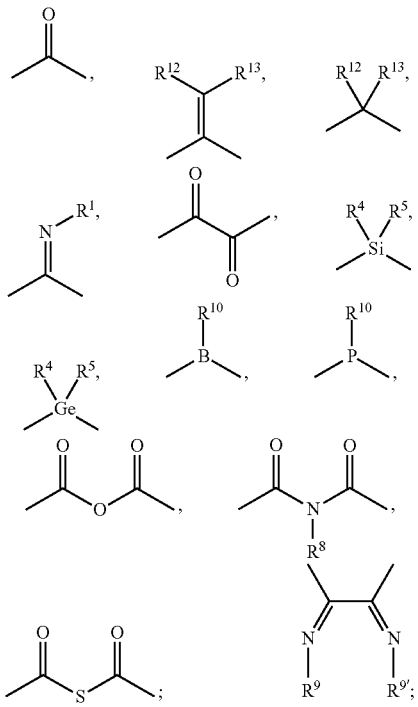

Y is selected from

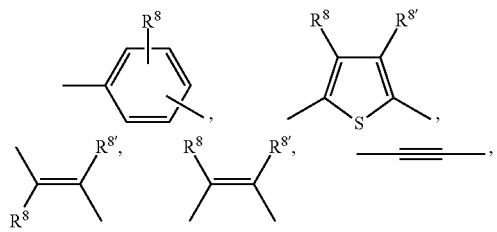

n ranges from 0 to 6;

R8 and R8' independently are H or as defined for R;

R9 and R9' together form a bridging group selected from

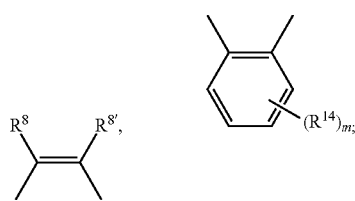

R10 is $C_1$-$C_{12}$alkyl, $C_5$-$C_{12}$cycloalkyl, phenyl, $C_7$-$C_{12}$alkylphenyl or $C_7$-$C_{12}$phenylalkyl, each of which is unsubstituted or substituted;

R11 is as defined for R8 or is OR8;

one of R12 and R13 may be hydrogen while the other, or both R12 and R13, are substituents; or both R12 and R13 are interlinked to form a divalent hydrocarbon residue of 2 to 25 carbon atoms which may be substituted and/or interrupted;

m is 0, 1, 2, 3 or 4, and R14 is a substituent, or 2 or 3 neighbouring residues R14 may be interlinked to form a divalent or trivalent hydrocarbon residue of 4 to 25 carbon atoms which may be substituted and/or interrupted; and any substituent, if present, is selected from halogen, OR, $C_1$-$C_{25}$alkyl, $C_2$-$C_{25}$alkenyl, $C_1$-$C_{25}$alkylthio, $C_1$-$C_{25}$acyl, $C_4$-$C_{10}$aryl, $C_1$-$C_9$heteroaryl, $C_3$-$C_{12}$cycloalkyl, $C_2$-$C_{11}$ heterocycloalkyl, $C_1$-$C_{25}$acyloxy, $C_5$-$C_{10}$aryloxy, $C_5$-$C_{12}$cycloalkyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R", PORR', PO(OR)R', $PO(OR)_2$, $PO(NHR)_2$, $PO(NRR')_2$, CN, $NO_2$, NHR, NRR', NH—NHR, NH—NRR', CONROH;

where R, R' and R" independently are selected from $C_1$-$C_{18}$alkyl, phenyl, cyclopentyl, cyclohexyl; and R may also be hydrogen.

6. Compound of claim 4, wherein $R^1$ and $R^{1'}$ are independently of each other H, halogen or $SiR^6R^4R^5$;

$R^2$ and $R^{2'}$ may be the same or different and are selected from $C_4$-$C_{18}$alkyl or $C_5$-$C_{25}$thienylalkyl or phenylalkyl; and in case that X is the bridging group

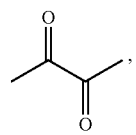

$R^2$ and $R^{2'}$ independently may also be hydrogen or $C_1$-$C_3$alkyl;

R4, R5, R6, R4', R5', R6' independently are selected from $C_1$-$C_{18}$alkyl;

R3 and R3', or R7 and R7', together, and X are a bridging group selected from

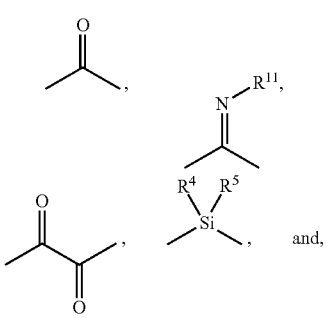

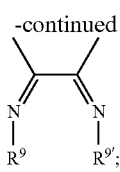

Y is

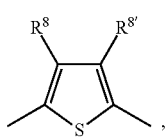

n ranges from 0 to 3;

R8 and R8' independently are H, $C_1$-$C_{18}$alkyl, phenyl, cyclopentyl, cyclohexyl;

R9 and R9' together form a bridging group selected from

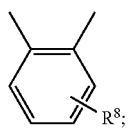

and

R11 is H, OH, $C_1$-$C_{18}$alkyl or $C_1$-$C_{18}$alkoxy.

7. Oligomer or polymer comprising at least 2 structural units of the formula

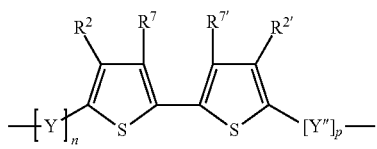

(XIII)

wherein $R^2$ and $R^{2'}$ may be the same or different and are selected from $C_1$-$C_{25}$alkyl, $C_3$-$C_{12}$cycloalkyl, $C_2$-$C_{25}$alkenyl, $C_2$-$C_{25}$alkynyl, $C_4$-$C_{25}$aryl, $C_5$-$C_{25}$alkylaryl or $C_5$-$C_{25}$aralkyl, each of which is unsubstituted or substituted; and in case that R7 and R7', together are the bridging group

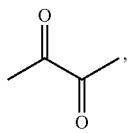

$R^2$ and $R^{2'}$ independently may also be hydrogen;

R7, R7' independently are $C_1$-$C_{25}$alkyl, $C_2$-$C_{25}$alkenyl, $C_2$-$C_{25}$alkynyl, $C_1$-$C_{25}$acyl, $C_2$-$C_{25}$alkoxycarbonyl, $C_1$-$C_{25}$acyloxy, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;

or R7 and R7', together are a bridging group selected from

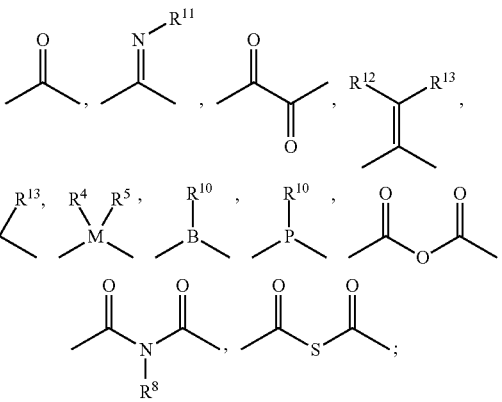

and, may also form a bridging group

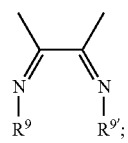

M is Si or Ge;

Y and Y" independently are selected from

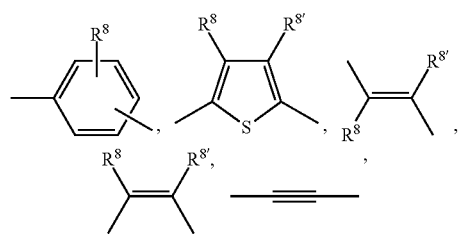

n and p independently range from 0 to 6;

R8 and R8' independently are H or a substituent;

R9 and R9' together form a bridging group selected from

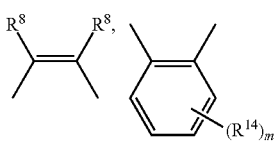

R10 is $C_1$-$C_{25}$alkyl, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;

R11 is as defined for R8 or is OR8;

one of R12 and R13 may be hydrogen while the other, or both R12 and R13, are substituents; or both R12 and R13 are interlinked to form a divalent hydrocarbon residue of 2 to 25 carbon atoms which may be substituted and/or interrupted;

m is 0, 1, 2, 3 or 4, and R14 is a substituent, or 2 or 3 neighbouring residues R14 may be interlinked to form a divalent or trivalent hydrocarbon residue of 4 to 25 carbon atoms which may be substituted and/or interrupted; and any substituent, if present, is selected from halogen, OR, $C_1$-$C_{25}$alkyl, $C_2$-$C_{25}$alkenyl, $C_1$-$C_{25}$alkylthio, $C_1$-$C_{25}$acyl, $C_4$-$C_{10}$aryl, $C_1$-$C_9$heteroaryl, $C_3$-$C_{12}$cycloalkyl, $C_2$-$C_{11}$ heterocycloalkyl, $C_1$-$C_{25}$acyloxy, or from the residues COR, CH=NR, CH=N—OH, CH=N—OR, COOR, CONHR, CONRR', CONH—NHR, CONH—NRR', SO$_2$R, SO$_3$R, SO$_2$NHR, SO$_2$NRR', SO$_2$NH—NHR, SO$_2$NH—NRR', S(O)R, S(O)OR, S(O)NHR, S(O)NRR', S(O)NH—NHR, S(O)NH—NRR', SiRR'R", PORR', PO(OR)R', PO(OR)$_2$, PO(NHR)$_2$, PO(NRR')$_2$, CN, NO$_2$, NHR, NRR', NH—NHR, NH—NRR', CONROH;

where R, R' and R" independently are selected from $C_1$-$C_{18}$alkyl, $C_1$-$C_{18}$haloalkyl, $C_5$-$C_{10}$aryl, $C_3$-$C_{12}$cycloalkyl;

and R may also be hydrogen.

8. Oligomer or polymer comprising at least 2 structural units of the formula (XIII),

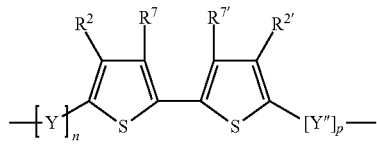

(XIII)

wherein;

$R^2$ and $R^{2'}$ may be the same or different and are selected from $C_1$-$C_{25}$alkyl, $C_3$-$C_{12}$cycloalkyl, $C_2$-$C_{25}$alkenyl, $C_2$-$C_{25}$alkynyl, $C_4$-$C_{25}$aryl, $C_5$-$C_{25}$alkylaryl or $C_5$-$C_{25}$aralkyl, each of which is unsubstituted or substituted, and R2 and/or R2' may also be halogen;

$R^2$ and $R^{2'}$ independently may also be hydrogen;

R7, R7' independently are $C_1$-$C_{25}$alkyl, $C_2$-$C_{25}$alkenyl, $C_2$-$C_{25}$alkynyl, $C_2$-$C_{25}$alkoxycarbonyl, $C_1$-$C_{25}$acyl, $C_1$-$C_{25}$acyloxy, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;

or R7 and R7', together are a bridging group selected from

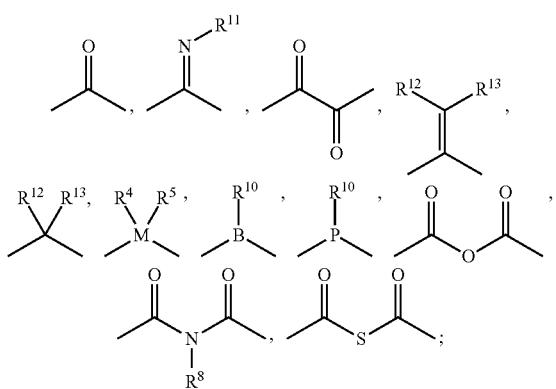

M is Si or Ge;

n and p independently range from 0 to 6;

Y is selected from

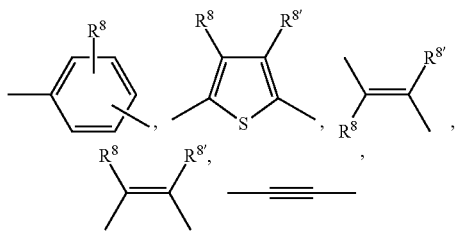

n ranges from 0 to 6;

R4 and R5 independently are selected from $C_1$-$C_{25}$alkyl, $C_3$-$C_{12}$cycloalkyl, $C_4$-$C_{25}$aryl, or $C_5$-$C_{25}$aralkyl;

and the neighbouring residues R4 and R5, may further be interlinked to form a divalent hydrocarbon residue of 4 to 25 carbon atoms which may be substituted and/or interrupted;

R8 and R8' independently are H or a substituent;

R9 and R9' together form a bridging group selected from

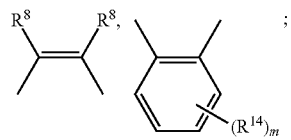

R10 is $C_1$-$C_{25}$alkyl, $C_3$-$C_{12}$cycloalkyl, $C_4$-$C_{25}$aryl, $C_5$-$C_{25}$alkylaryl or $C_5$-$C_{25}$aralkyl, each of which is unsubstituted or substituted;

m is 0, 1, 2, 3 or 4;

R11 is as defined for R8 or is OR8;

one of R12 and R13 may be hydrogen while the other, or both R12 and R13, are substituents; or both R12 and R13 are interlinked to form a divalent hydrocarbon residue of 2 to 25 carbon atoms which may be substituted and/or interrupted;

and R14 is a substituent, or 2 or 3 neighbouring residues R14 may be interlinked to form a divalent or trivalent hydrocarbon residue of 4 to 25 carbon atoms which may be substituted and/or interrupted; and any substituent, if present, is selected from halogen, OR, $C_1$-$C_{25}$alkyl, $C_2$-$C_{25}$alkenyl, $C_1$-$C_{25}$alkylthio, $C_1$-$C_{25}$acyl, $C_4$-$C_{10}$aryl, $C_1$-$C_9$heteroaryl, $C_3$-$C_{12}$cycloalkyl, $C_2$-$C_{11}$heterocycloalkyl, $C_1$-$C_{25}$acyloxy, or from the residues COR, CH=NR, CH=N—OH, CH=N—OR, COOR, CONHR, CONRR', CONH—NHR, CONH—NRR', SO$_2$R, SO$_3$R, SO$_2$NHR, SO$_2$NRR', SO$_2$NH—NHR, SO$_2$NH—NRR', S(O)R, S(O)OR, S(O)NHR, S(O)NRR', S(O)NH—NHR, S(O)NH—NRR', SiRR'R", PORR', PO(OR)R', PO(OR)$_2$, PO(NHR)$_2$, PO(NRR')$_2$, CN, NO$_2$, NHR, NRR', NH—NHR, NH—NRR', CONROH;

where R, R' and R" independently are selected from $C_1$-$C_{25}$alkyl, $C_1$-$C_{25}$haloalkyl, $C_5$-$C_{10}$aryl, $C_3$-$C_{12}$cycloalkyl;

and R may also be hydrogen;

provided that if R7 and R7' together are —CO—, at least one of R2 and R2' contains at least 2 carbon atoms.

9. Polymer obtained by homopolymerization of a compound of the formula

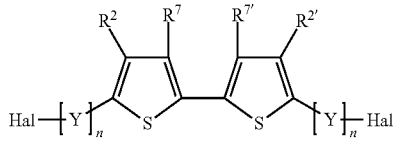

(XIV)

wherein Hal stands for halogen and all other symbols are as defined in claim 4, or by copolymerization of a compound of the formula (XIV) with a further monomer.

10. Compound according to claim 4, wherein any substituent, if present, is selected from halogen, OR, $C_1$-$C_{25}$alkyl, $C_2$-$C_{25}$alkenyl, $C_1$-$C_{25}$alkylthio, $C_1$-$C_{25}$acyl, $C_4$-$C_{10}$aryl, $C_1$-$C_9$heteroaryl, $C_3$-$C_{12}$cycloalkyl, $C_2$-$C_{11}$heterocycloalkyl, $C_1$-$C_{25}$acyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R", PORR', PO(OR)R', $PO(OR)_2$, $PO(NHR)_2$, $PO(NRR)_2$, CN, $NO_2$, NHR, NRR', NH—NHR, NH—NRR', CONROH;

where R, R' and R" independently are selected from $C_1$-$C_{18}$alkyl, $C_1$-$C_{18}$haloalkyl, $C_5$-$C_{10}$aryl, $C_3$-$C_{12}$cycloalkyl;

and R may also be hydrogen.

11. A semiconductor device, comprising a compound according to claim 4.

12. A semiconductor device of claim 11 containing the compound of the formula (XI) and/or (XII) according to claim 4 as a layer, having a thickness from the range 5 to 1000 nm, on a rigid or flexible solid substrate.

13. Process for the preparation of an organic semiconductor device, which process comprises applying a solution and/or dispersion of a compound of the formula (XI) and/or (XII) according to claim 4, in an organic solvent to a suitable substrate and removing the solvent.

14. A charge-transport material, semiconducting material, electrically conducting material, photoconducting material, light emitting material, surface-modifying material, electrode material in a battery, alignment layer, or in an organic field effect transistor, integrated circuit, thin film transistor, display, RFID tag, electro- or photoluminescent device, backlight of a display, photovoltaic or sensor device, charge injection layer, Schottky diode, memory device (e.g. FeFET), planarising layer, antistatics, conductive substrate or pattern, photoconductor, or electrophotographic application or recording material comprising the compound of formula (XI) and/or (XII) according to claim 4.

15. A charge-transport material, semiconducting material, electrically conducting material, photoconducting material, light emitting material, surface-modifying material, electrode material in a battery, alignment layer, or in an organic field effect transistor, integrated circuit, thin film transistor, display, RFID tag, electro- or photoluminescent device, backlight of a display, photovoltaic or sensor device, charge injection layer, Schottky diode, memory device (e.g. FeFET), planarising layer, antistatics, conductive substrate or pattern, photoconductor, or electrophotographic application or recording material comprising the oligomer or polymer according to claim 7.

16. Process for the preparation of an organic semiconductor device, which process comprises applying a solution and/or dispersion of an oligomer or polymer according to claim 7 in an organic solvent to a suitable substrate and removing the solvent.

17. The semiconductor device according to claim 11, wherein the device is a diode, a photodiode, an organic field effect transistor and/or a solar cell, or a device containing a diode and/or a photodiode and/or an organic field effect transistor, and/or a solar cell.

18. A semiconductor device, comprising an oligomer or polymer according to claim 7.

* * * * *